(12) United States Patent
Ohnemus et al.

(10) Patent No.: US 9,378,336 B2
(45) Date of Patent: Jun. 28, 2016

(54) OPTICAL DATA CAPTURE OF EXERCISE DATA IN FURTHERANCE OF A HEALTH SCORE COMPUTATION

(75) Inventors: Peter Ohnemus, Küsnacht (CH); Andre Naef, Zurich (CH)

(73) Assignee: dacadoo ag, Zurich (CH)

( * ) Notice: Subject to any disclaimer, the term of this patent is extended or adjusted under 35 U.S.C. 154(b) by 280 days.

(21) Appl. No.: 13/423,051

(22) Filed: Mar. 16, 2012

(65) Prior Publication Data

US 2012/0296455 A1 Nov. 22, 2012

Related U.S. Application Data

(60) Provisional application No. 61/486,658, filed on May 16, 2011.

(51) Int. Cl.
*G06Q 50/22* (2012.01)
*G06Q 50/24* (2012.01)
*G06F 19/00* (2011.01)

(52) U.S. Cl.
CPC ......... *G06F 19/3481* (2013.01); *A63B 2220/05* (2013.01); *A63B 2220/807* (2013.01); *G06F 19/3487* (2013.01)

(58) Field of Classification Search
CPC .... G06Q 50/22; G06Q 50/24; G06F 19/3481; G06F 19/3475; G06F 19/3437; G06F 19/322
USPC ........................................................ 705/2, 3
See application file for complete search history.

(56) References Cited

U.S. PATENT DOCUMENTS

| | | | |
|---|---|---|---|
| 6,110,109 A | 8/2000 | Hu et al. | |
| 6,514,199 B1 | 2/2003 | Alessandri | |
| 6,616,578 B2 | 9/2003 | Alessandri | |
| 6,702,719 B1 * | 3/2004 | Brown et al. | 482/8 |
| 7,628,730 B1 | 12/2009 | Watterson et al. | |
| 8,075,450 B2 | 12/2011 | Fabbri et al. | |
| 8,712,510 B2 * | 4/2014 | Quy | 600/520 |
| 2002/0047867 A1 * | 4/2002 | Mault et al. | 345/810 |
| 2002/0055418 A1 | 5/2002 | Pyles et al. | |
| 2005/0076301 A1 | 4/2005 | Weinthal | |
| 2005/0165618 A1 | 7/2005 | Nerenberg | |

(Continued)

FOREIGN PATENT DOCUMENTS

| | | |
|---|---|---|
| EP | 0709058 | 5/1996 |
| EP | 1087824 | 4/2001 |

(Continued)

*Primary Examiner* — Maroun Kanaan
(74) *Attorney, Agent, or Firm* — Leason Ellis LLP

(57) ABSTRACT

A computer implemented method for managing health-related data captures an image from a display of an exercise machine using a camera, has the images processed to extract the text data from the captured images, and analyzes the text data to identify information relating to extrinsic physical activity performed by a person at the exercise machine. The results are stored in memory and a profile specific to the person is updated. The profile comprises a log of past exercise activity that allows the person to track his or her activity and progress and overall health. The profile can be accessed by the person through a portal such as using a smart phone or a computer program or web browser. The results can be combined with other data to arrive at a health score which can be published through the portal while personal data remains masked from public inspection.

10 Claims, 16 Drawing Sheets

(56) References Cited

U.S. PATENT DOCUMENTS

| | | |
|---|---|---|
| 2005/0228692 A1 | 10/2005 | Hodgdon |
| 2005/0289590 A1 | 12/2005 | Cheok et al. |
| 2007/0161868 A1 | 7/2007 | Root |
| 2007/0168230 A1 | 7/2007 | Roman |
| 2007/0276203 A1* | 11/2007 | Day ............................ 600/301 |
| 2008/0089666 A1 | 4/2008 | Aman |
| 2009/0105047 A1 | 4/2009 | Guidi et al. |
| 2009/0105550 A1 | 4/2009 | Rothman et al. |
| 2009/0156363 A1 | 6/2009 | Guidi et al. |
| 2009/0163774 A1 | 6/2009 | Thatha et al. |
| 2010/0004945 A1 | 1/2010 | Petratos et al. |
| 2010/0004947 A1 | 1/2010 | Nadeau et al. |
| 2010/0082362 A1 | 4/2010 | Salsbury et al. |
| 2011/0213664 A1* | 9/2011 | Osterhout et al. ......... 705/14.58 |
| 2012/0094649 A1 | 4/2012 | Porrati et al. |
| 2012/0179665 A1* | 7/2012 | Baarman et al. .............. 707/709 |

FOREIGN PATENT DOCUMENTS

| | | |
|---|---|---|
| EP | 1259153 | 11/2002 |
| EP | 1400264 | 3/2004 |
| EP | 2025368 | 2/2009 |
| WO | WO 2004/095195 | 11/2004 |
| WO | WO 2007/112034 | 10/2007 |
| WO | WO 2009/026156 | 2/2009 |

\* cited by examiner

Fig. 6d

OPTICAL DATA CAPTURE OF EXERCISE DATA IN FURTHERANCE OF A HEALTH SCORE COMPUTATION

CROSS-REFERENCE TO RELATED PATENT APPLICATIONS

The present application claims priority to and the benefit of U.S. Patent Application No. 61/486,658, filed May 16, 2011, which is hereby incorporated by reference in its entirety.

FIELD OF THE INVENTION

The present invention concerns a device for tracking a route and determining energy expenditure of a person along that route. More particularly, the invention concerns a device that collects information about a person, details of the exercise event, and horizontal and vertical distance data of a route to calculate energy expenditure of a person traveling along the route.

BACKGROUND OF THE INVENTION

As a person engages in exercise activity, it is useful to the person to be able to know how much energy the person exerted during that activity. Typically, exercise equipment in gyms, such as treadmills and stationary bikes, is capable of calculating and presenting the energy expended by the person during the exercise activity in the form of calories burned data. The user only needs to enter their weight information for the machine to estimate the calories burnt. However, these machines operate in a controlled environment. The type of activity that can be performed on the machine (biking or running) is dictated by the type of machine (bike or treadmill). The speed and elevation (angle of treadmill or resistance on bike) is controlled by the machine and thus known by the machine. Moreover, the "terrain" is uniform on these machines because the exercise surfaces do not change (the walking surface of the treadmill does not change to sand). Thus, it is relatively easy for these machines to calculate the energy expended in these controlled environments. These machines are well suited to report exercise information pertaining to the user however, one drawback is that the information is transient. The information is displayed by the machine for a short while, and in most instances personal logging of information is only possible on a single machine. In more advanced systems at gyms, there can be a logging system that can capture workout information across multiple machines at the gym, however this system is limited to that particular gym location or chain of gyms. It is desirable to be able to log workouts across a variety of machines and in a multitude of locations such as at home or at the gym or while on vacation.

Many people desire exercise outdoors and do not want to be confined to a machine in a gym. Outdoor exercising is fraught with many variables, such as changes in terrain. Moreover, the distance traveled, the speed, and the changes of elevation are not controlled by a machine. This presents a layer of difficulty in determining the energy expended on an outdoor exercise route because these parameters must be measured. With the proliferation of smart, mobile electronic devices, such as smart phones, measuring these parameters has become easier. Smart phones typically have the ability to determine position using GPS modules. Software applications that use the GPS feature of the phones can calculate distance traveled and speed during an exercise route. The software applications can also use the GPS feature to calculate the changes in elevation during the exercise route. If the user enters his or her weight, the software applications can calculate the calories burned during the exercise route.

These existing applications have several drawbacks, however. For example, these systems rely upon GPS to determine changes in elevation. While GPS can determine latitude and longitude relatively accurately, GPS systems are less accurate at calculating elevation. Accordingly, systems that rely upon GPS to determine elevation changes during the exercise route, which is in turn used to calculate calories burned, suffer from accuracy issues. Moreover, these systems are limited to a particular activity, such as running. These systems cannot be used for different activities, such as running, biking, skiing, etc. These systems are also limited in the information about the activity that is considered which can greatly affect the energy expenditure calculations.

The present invention addresses these and other problems.

DESCRIPTION OF THE DRAWING FIGURES

FIGS. 6a-6e are screen shots of a user interface according to one embodiment of the invention;

SUMMARY OF THE INVENTION

Figure 1A:
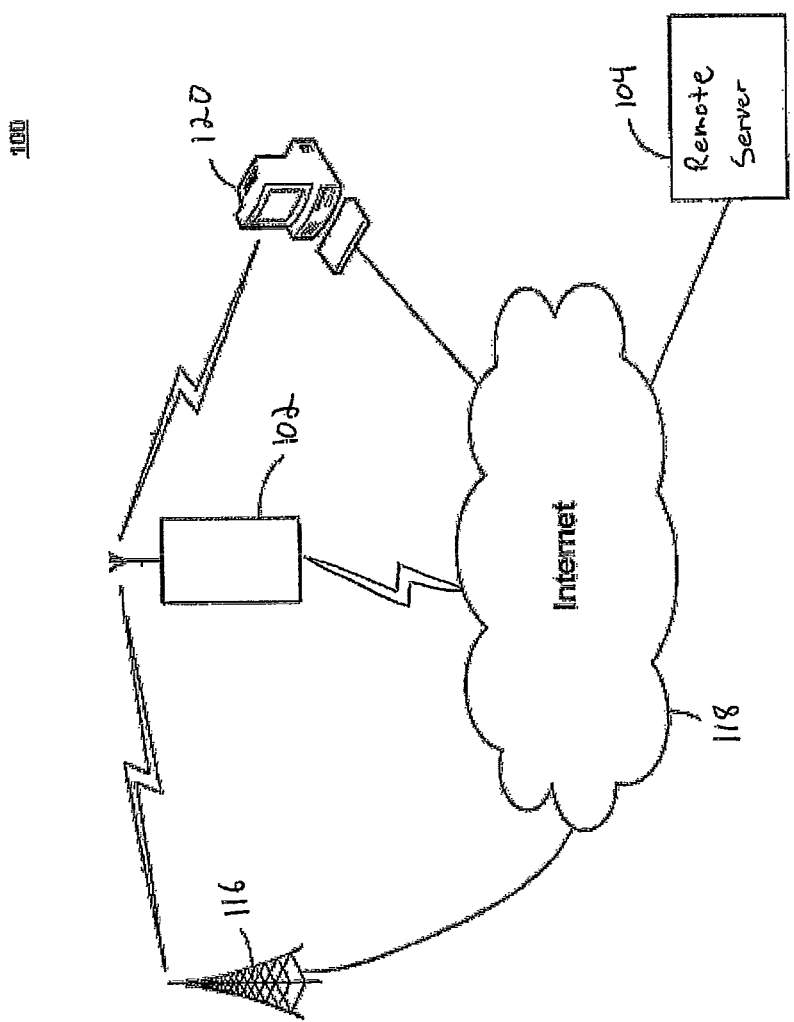
FIG. 1A illustrates an exemplary diagram of a mobile electronic device in wireless communication.

According to an aspect of the present invention, there is provided a computer implemented method for managing health-related data. The method includes receiving data into a memory relating to a plurality of extrinsic physical activity parameters and capturing an image from a display that is coupled to an exercise machine. The image can be captured, by example, with a smart phone camera. According to this method the images are then processed to extract the text data from the captured images, and the extracted text is analyzed to identify information relating to the extrinsic physical activity performed by the person using the system on the exercise machine. The results are stored in memory and a profile specific to the person is updated. The profile comprises a log of past exercise activity that allows the person to track his or her activity and progress and overall health. The profile can be accessed by the person through a portal such as using a smart phone or a computer program or web browser.

In another arrangement, the text can be extracted using an optical character recognition algorithm which distinguishes text characters from other image data and records the text character and its location and other spatial properties.

In another arrangement the text extracted from the captured image can be analyzed to identify sequences in the text. This can be done by identifying characters that are in proximity and of the same type (i.e. letter or number) and grouping those characters together. Sequenced data can be further manipulated and analyzed by the processor and sorted into categories such as numbers, duration and units. In addition, the spatial relationships between various sequences can be determined by the system.

According to a further aspect of such a method, the image can be analyzed to identify the manufacturer's brand of the exercise machine. In addition, the method can further comprise the step of extracting text from a limited area of the image as dictated by the brand of the exercise machine.

According to an aspect of the present invention, there is provided a computer implemented method for processing private health related data into a masked numerical score suitable for publishing. The method comprises receiving data into a memory on a plurality of intrinsic medical parameters and extrinsic physical activity parameters of a user. The received data and weighting factors are stored in the memory. The received data is processed by executing code in a processor that configures the processor to apply the weighting factors to the intrinsic medical parameters and the extrinsic physical activity parameters. The weighting factors for at least the extrinsic physical activity parameters include a decay component arranged to reduce the relative weight of the extrinsic physical activity parameters for a physical activity in dependence on at least one factor associated with the user. The processed data concerning the intrinsic medical parameters and the extrinsic physical activity parameters are transformed by further code executing in the processor into a masked composite numerical value in which the code is operative to combine the weighted parameters in accordance with an algorithm. The masked composite numerical value is automatically published to a designated group via a portal (such as a social web site) using code executing in the processor and free of any human intervention. Meanwhile, the collected information concerning the intrinsic medical parameters and the extrinsic physical activity parameters is maintained private.

According to a further aspect of such a method as can be implemented in a particular embodiment thereof, the factor associated with the user can be an age or an age range of the user such that the decay component reduces the relative weight of the extrinsic physical activity parameters for a first user of a first age or age range differently than a second user of a second age or age range.

According to still another aspect of such a method as can be implemented in a particular embodiment thereof, the published masked composite numerical value can comprise an average of a group of users to arrive at a group composite numerical value determination using further code executing in the processor.

According to an additional aspect of the present invention, there is provided a computer implemented health monitoring system which comprises a communication unit operable to receive data on a plurality of intrinsic medical parameters and extrinsic physical activity parameters of a user. A memory is arranged to store the received data and to store weighting factors. Also, a processor is arranged to process the received data by executing code that configures the processor to apply the weighting factors to the intrinsic medical parameters and the extrinsic physical activity parameters. The weighting factors for at least the extrinsic physical activity parameters include a decay component arranged to reduce the relative weight of the physical activity parameters for a physical activity in dependence on at least one factor associated with the user. The processor is further arranged to execute code to transform the processed data concerning the intrinsic medical parameters and the extrinsic physical activity parameters into a masked composite numerical value using the processor by combining the weighted parameters in accordance with an algorithm. A portal is arranged to publish the masked composite numerical value to a designated group while maintaining the collected information concerning the intrinsic medical parameters and the extrinsic physical activity parameters private.

Such a system can preferably be configured so that the factor associated with the user can be an age or an age range of the user such that the decay component reduces the relative weight of the extrinsic physical activity parameters for a first user of a first age or age range differently than a second user of a second age or age range.

DETAILED DESCRIPTION OF CERTAIN EMBODIMENTS OF THE INVENTION

The following detailed description, which references to and incorporates the drawings, describes and illustrates one or more specific embodiments of the invention. These embodiments, offered not to limit but only to exemplify and teach the invention, are shown and described in sufficient detail to enable those skilled in the art to practice the invention. Thus, where appropriate to avoid obscuring the invention, the description may omit certain information known to those of skill in the art.

Figure 1B:
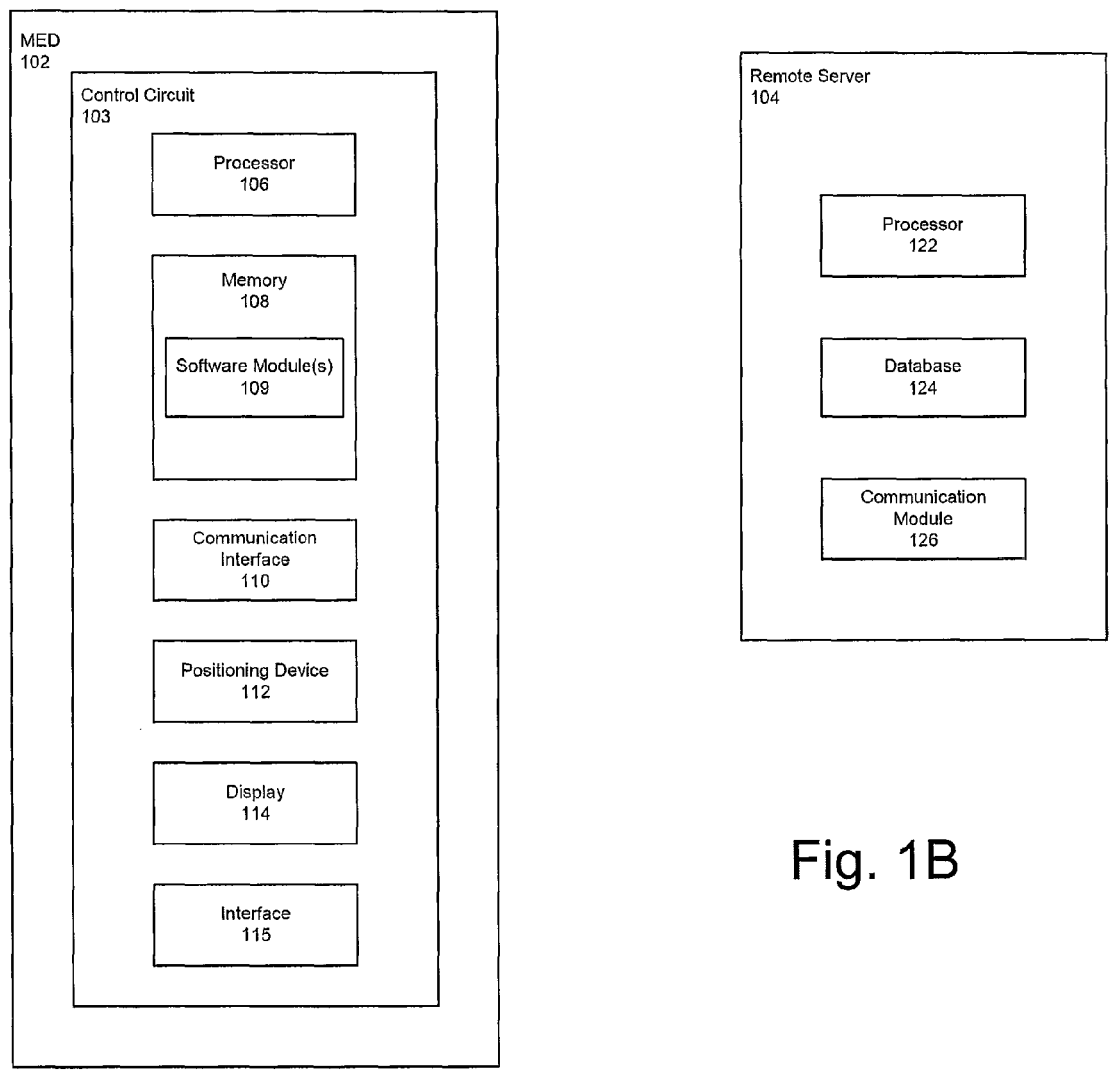
FIG. 1B is a block diagram illustrating certain components of the mobile electronic device and a remote server.
Figure 1C:
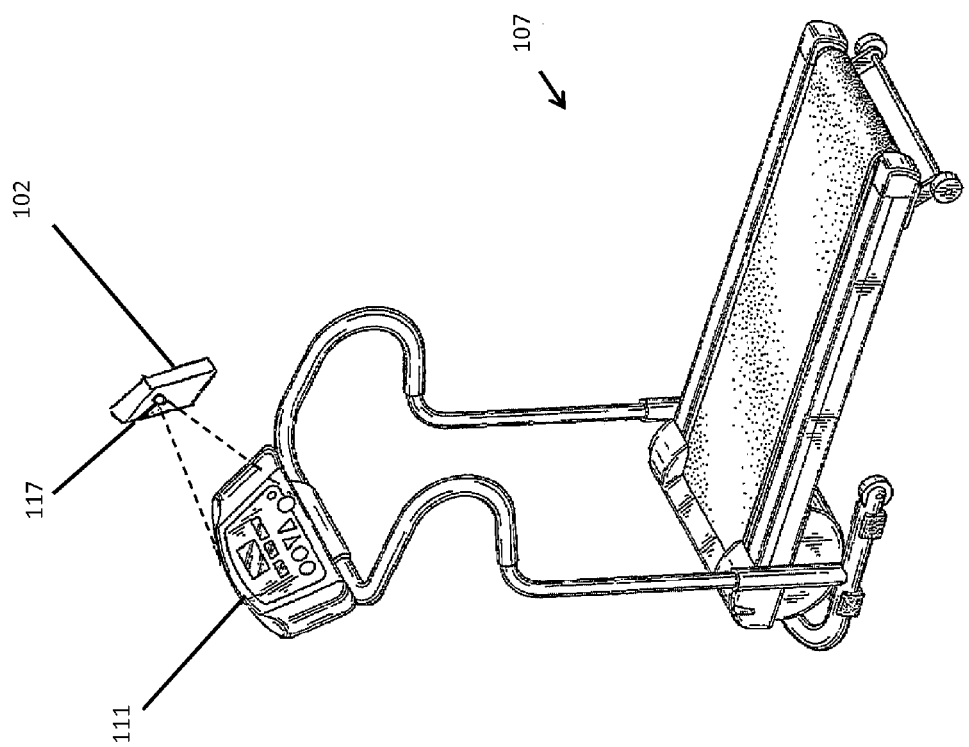
FIG. 1C is an exemplary diagram of a system for managing health related data.

In one implementation, referring to FIGS. 1A and 1B and 1C, a system 100 for determining the energy expenditure of a person includes a mobile electronic device 102 and a remote server 104.

The mobile electronic device 102 can be a cell phone, personal digital assistant, smart phone, tablet computing device, or other portable electronic device. Mobile electronic device 102 includes a control circuit 103 which is operatively connected to various hardware and software components that serve to enable determination of energy expenditure of a person traveling along a route and/or determine extrinsic physical activity parameters of a person exercising on an exercise machine 107, as discussed in greater detail below. The control circuit 103 is operatively connected to a processor 106 and a memory 108. Preferably, memory 108 is accessible by processor 106, thereby enabling processor 106 to receive and execute instructions stored on memory 108.

One or more software modules 109 are encoded in memory 108. The software modules 109 can comprise a software program or set of instructions executed in processor 106. Preferably, the software modules 109 make up an exercise monitoring application that collects data, i.e. extrinsic physical activity information, that can used to calculate energy expenditure, and perform other functions, that is executed by processor 106. During execution of the software modules 109, the processor 106 configures the control circuit 103 to gather information about the person and the person's exercise route, communicate position details about the exercise route in order to receive elevation details, and other functions, as discussed in greater detail below. During execution of the modules, the processor 106 can also configure the control circuit to gather image data from a camera. It should be noted that while FIG. 1B depicts memory 108 on control circuit 103, in an alternate arrangement, memory 108 can be practically any storage medium (such as a hard disk drive, flash memory, etc.) that is operatively connected to the control circuit 103, even if not oriented on the control circuit as depicted in FIG. 1B.

An interface 115 is also operatively connected to control circuit 103. The interface 115 preferably includes one or more input device(s) such as a switch, knob, button(s), key(s), touchscreen, etc. Interface 115 is operatively connected to the control circuit 103 and serves to facilitate the capture of certain profile information and details about the exercise event from the user, as discussed in greater detail below. By way of example, input device of interface 115 can be a touch screen display. Accordingly, the display 114 is used to display a graphical user interface, which displays various data and provide "forms" that include fields that allow for the entry of additional information by the user. Touching the touch screen interface 115 at locations corresponding to the display of the graphical user interface allows the person to interact with the device to enter data, change settings, control functions, etc. So, when the touch screen is touched, interface 115 communicates this change to control circuit 103, and settings can be changed or user entered information can be captured and stored in the memory 108.

The display 114 includes a screen or any other such presentation device which enables the user to view various options and parameters, and select among them using the interface 115 referenced above. In yet another arrangement, either one or both of the interface 115 and display 114 can be implemented in a non-visual and/or non-tactile fashion, such as by using a series of audio menus and/or voice commands/prompts to select and/or define settings, provide information about the user and the exercise event, and/or control the functions of the system.

In one arrangement, interface 115 further enables the defining of settings and the entry of information by initiating and/or maintaining one or more communication sessions with an external device that is communicatively linked with mobile device 102. In one arrangement, interface 115 can connect with an external personal computer (PC) through a USB connection, Bluetooth connection, or any other connection/communication medium. The user can then utilize the connected PC to define user settings, profile data, etc., and/or upload or otherwise communicate new settings, profile data, etc., which the user has previously defined and/or has obtained from an external source (such as the Internet). In another arrangement, interface 115 can connect with an external storage device, such as a USB flash drive, and receive one or more settings that are stored thereupon. In yet another arrangement, interface 115 via communication interface 110 can connect to one or more external servers through a network connection. For instance, interface 115 can utilize a pre-existing network connection, such as an Internet connection, via communication interface 110 using a wireless connection. In doing so, the interface can connect with various remote servers which contain settings that are available for users to download. The user can download one or more desired settings and store them in memory 108. This functionality of interface 115, which enables the user to obtain and/or update the set of user settings, profile data, event data, etc., stored in memory 108, is of particular utility when used to obtain and/or update settings pertaining to specific exercise equipment (e.g., weight of bike is pre-stored) or exercise route information (e.g., details about a person's favorite exercise route, such as the terrain information, etc. can be pre-stored so that they do not have to be reentered every time the person follows the same route).

A positioning device 112 is operatively connected to control circuit 103. The positioning device 112 can be a global positioning system (GPS) circuit or a positioning system that relies on triangulation between cell phone towers in order to determine position. The positioning device 112 permits the determination of the location of the mobile device 102 and hence the position of the person. Using the positioning device 112 the position coordinates (e.g., latitude and longitude) of the person can be determined.

A communication interface 110 is operatively connected to control circuit 103. The communication interface 110 can be a cellular communication circuit allowing communication with a cellular network 116, a Wi-Fi communication circuit allowing communication directly to the internet 118 through a Wi-Fi connection, and/or a circuit allowing communication with a computer terminal 120, such as a Bluetooth® circuit and/or circuit allowing wired communication.

The control circuit 103 can also be operatively connected to a camera 117. The camera 117 can be any type of digital camera including but not limited to a camera found on a smart phone or cell phone. The camera can be used to capture digital images of the user display 111 of an exercise machine 107 that displays exercise activity related information. By way of example, the information can be related to how much energy was expended by the person, in the form of calories burned data or other unit of energy, the information can also relate to the distance traveled while on the machine. The control circuit is configured to store the digital images that are captured by the camera in memory 108. The processor 106 is configured to analyze the images and to extract extrinsic physical activity parameters relating to the user's exercise activity.

Referring to FIG. 1A, an exemplary diagram illustrates the mobile electronic device 102 preferably in wireless communication with communication network 116, such as a cellular communication network. Mobile device 102's communication with communication network 116 facilitates connection to the internet 118. Remote server 104 is also connected to the internet 118. Accordingly, the mobile electronic device 102 can communicate with and transmit data to and receive data from the remote server 104 via communication network 116 and the internet 118.

The mobile electronic device 102 can also communicate with a computer terminal 120. Computer terminal 120 can be a personal computer, for example. The mobile electronic device 102 can communicate with the computer terminal 120 via a Wi-Fi or Bluetooth connection, for example. The mobile electronic device 102 can also communicate with the computer terminal 120 via a wired connection, using a USB tether, for example. The computer terminal 120 is connected to the internet 118. Thus, the mobile electronic device 102 can communicate with the remote server 104 via a computer terminal 120. The mobile electronic device 102 can also communicate with the internet 118 through its communication interface 110 (e.g., Wi-Fi) and thus connect to the remote server 104.

The server 104 includes a processor 122, a database 124, and a communication interface 126. The database 124 includes topographic data. The topographic data can be in the form of topographic maps that include contour lines and elevation data. Each contour line represents an interval of elevation. For example, if the contour lines represent an interval of ten feet, crossing ten contour lines between two points on a topographic map represents a change of 100 feet of elevation. The distance between the contour lines on the map represents slope of the terrain. The closer the contour lines are together, the greater the slope of the terrain. Topographic maps can be digital data that includes elevations at know coordinate points on the map. Topographic maps and data can be used to determine the elevation at a given position. As discussed in more detail below, the remote server 104 can receive position coordinate data from mobile electronic device 102, correlate the position coordinates with the topographic map data, and determine the elevation at that position. The remote server 104 can transmit the elevation value that corresponds to the position coordinate back to the mobile electronic device 102.

The operation of the mobile device 102 and the various elements described above will be appreciated with reference to the method for calculating the energy exerted by a person along an exercise route, as described below, in conjunction with FIG. 2.

Figure 2:
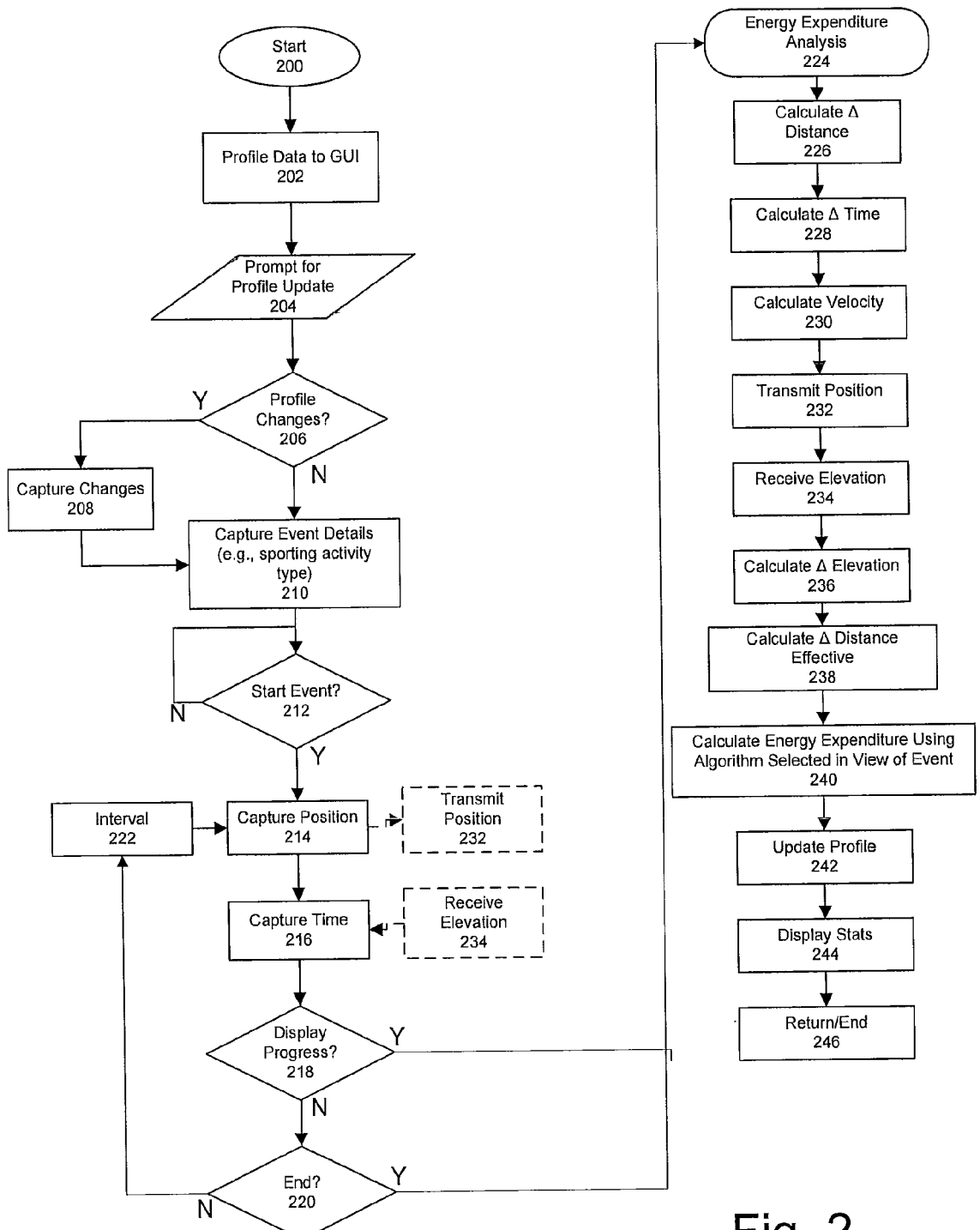
FIG. 2 is a flowchart illustrating a process of calculating energy expenditure.

Referring now to FIG. 2, a flow diagram illustrates functionality suitable for capturing information about a person, the person's route, and other information, in order to determine the amount of energy the person expends traveling along that route. The system 100 can be used by the person to calculate the energy expended by the person as they travel along a route, such as an exercise route. It should be appreciated that several of the logical operations described herein are implemented (1) as a sequence of computer implemented acts or program modules running on mobile device 102 and/or (2) as interconnected machine logic circuits or circuit modules within the mobile device 102. The implementation is a matter of choice dependent on the requirements of the device (e.g., size, energy, consumption, performance, etc.). Accordingly, the logical operations described herein are referred to variously as operations, structural devices, acts, or modules. Various of these operations, structural devices, acts and modules can be implemented in software, in firmware, in special purpose digital logic, and any combination thereof. It should also be appreciated that more or fewer operations can be performed than shown in the figures and described herein. These operations can also be performed in a different order than those described herein.

At step 200 a person initiates the device for calculating energy expenditure. Preferably, a person initiates the system prior to commencing exercise activity that involves traveling along a route (e.g., walking, running, hiking, biking, snow shoeing, cross country skiing, etc.).

At step 202, the person's profile is displayed. A profile contains various physiological and other health related information about the person. The profile information can include the person's age, weight, height, body mass index, physical fitness information (e.g., information about a person's ability to complete physical tasks (running speed, endurance, weight lifting capability, etc.)), medical history (e.g., medical conditions, such as, diabetes, heart disease, high blood pressure, cholesterol levels, lipid levels, etc.). At least some or all of this information can be used in the calculation to determine the energy the person exerted as a result of traveling the route, as will be discussed in further detail below.

The person is prompted to update their profile at step 204. For example, a person may have lost or gained weight since the last time their profile was updated. Accordingly, the person is presented an opportunity to correct that information and the profile changes are captured at step 208. If the profile is missing data or is completely empty (e.g., the first use of the system by this person), the person can supply the required information to populate the profile.

At step 210, details about the exercise event are captured. For example, environmental data, such as temperature data, wind speed and wind direction data, humidity data, etc., can be captured. The system can prompt the mobile electronic device 102 to determine the position of the mobile electronic device using the positioning device 112. The system can then connect to the internet using its communication interface 110 and transmit the position data to a weather database or weather service website available on the internet. The mobile electronic device 102 can then receive the environmental data from the weather service that correlates to that position. The person can also manually enter the environmental condition information. The environmental conditions can affect the energy exerted during the exercise event. For example, high temperatures can cause a person to exert more energy during exercise or the direction and speed of the wind (i.e., tail wind or head wind) can affect energy exertion, especially during activities such as biking. The environmental data can be used to generate a weighting factor that will increase or decrease certain values in the energy expenditure calculation. The environmental data can also be used as a variable in the energy expenditure calculation (e.g., wind speed in the calculation for biking, as discussed in more detail below).

In addition, the person can be prompted to enter additional information about the exercise activity they are performing. For example, they can indicate whether they are walking, running, biking, hiking, cross country skiing, snow shoeing, skating, skateboarding, etc. More energy will be exerted running a given distance than biking a given distance and the algorithms used to calculate that energy expenditure may be different. Accordingly, selecting an activity type assigns a parameter value and the system checks the parameter value to select the proper algorithm to determine energy expenditure. In addition, selecting the type activity can control the functioning of the system. For example, sports such as tennis, squash, baseball, football, soccer, etc., are typically played on flat fields of limited dimensions. These types of activities typically do not involve changing elevation as the person moves along the field. Thus, elevation measurement becomes less important in determining energy expended. Accordingly, a parameter can be set to a zero value for activities that are defined as not involving elevation change (e.g., soccer) and a non-zero value for activities that are defined as potentially involving elevation changes (e.g., running). The system can then check the parameter, and if it is zero, the system skips the procedure of transmitting location information to a remote server and receiving elevation information (steps 232 and 234, discussed in more detail below), and assumes that the elevation change is zero. If the parameter is non-zero, the system performs the elevation determination steps. In addition, the type activity can also control how the system determines distance traveled. For example, tennis is performed on a relatively confined court and using GPS alone to determine distance traveled associated with moving back and forth across the court may not produce the most accurate results. Thus, the system can also use an accelerometer to determine the amount of movement of the person. The type of activity selected has a predetermined parameter value associated with it, and depending on the value, the system can use different algorithms and methods for determining distance traveled using accelerometer data.

The person can also enter information about the route terrain, such as whether the ground surface is paved road, gravel road, dirt road, woods trail with woodland debris, loose gravel, loose sand, etc. The type of terrain can affect the energy exerted by a person along a route. For example, more energy is exerted running on sand than running on a paved road. The system can have stored values associated with the type of terrain that can be used in the calculation of the energy expenditure. The person can also enter information about the type of equipment they are using, such as whether they are riding a mountain bike, which has thick, rough tires with lower pressure and hence a higher resistance, or a road bike, which has thin, smooth tires at high pressure and hence a lower rolling resistance. For example, the system can have stored friction values for tires or different widths, diameters, tread types, and inflation pressures. The person can also indicate if they are carrying any equipment, such as a backpack with supplies, and the weight of the pack. Thus, terrain, environmental, and equipment information can be included in the calculation (either as a weighting factor or a variable) to determine energy expenditure in order to increase the accuracy of the expenditure calculation.

At step 212, the person, through the interface of the mobile electronic device 102, indicates at the start of the event. Doing so indicates that the person has started their exercise and will be progressing along an exercise route. Accordingly, at step 214 the position of the person is captured using the positioning device 112 of the mobile electronic device 102. As discussed above, mobile electronic device 102 includes a positioning device 112 that determines the position of the person. The positioning device 112 can be a global positioning system (GPS) module or a positioning system that relies on triangulation between cell phone towers in order to determine position. The positioning device 112 permits the mobile electronic device 102 to determine the position coordinates (e.g., latitude and longitude) of the mobile electronic device, and hence the person carrying the mobile electronic device.

At step 216, the time is captured that corresponds to the time at which the position was captured in step 214. The position and corresponding time data are then stored in the memory 108 of the mobile electronic device 102. This creates a trackpoint, which is a record of the person's position and the time the person was at that position. These trackpoints can be used to determine the distance traveled and the speed of the person during the exercise event, as discussed further herein.

At step 218, the person is presented with an option to display their current progress during the exercise event. If the person does not request an intermediate progress display, the person can continue exercising.

The person can indicate whether the exercise event is complete, at step 220. If the event is not complete, the system optionally waits for an interval to elapse at step 222, before returning to the capture position step 214. The interval can be a distance interval and/or a time interval. The GPS module can create a notification that the device has moved a certain distance, which satisfies the "interval" at step 222 and caused the position to be captured at step 214. In addition, or in the alternative, the interval can be a time interval and after the predetermined interval has elapsed, the system proceeds to step 214 and the position is captured. The time interval between successive position captures can be set for a longer time interval in order to reduce the number of processing cycles and hence preserve power and battery life. The time interval can also be set for a short time if more data points are desired, which will result in more precise information about the person's exercise route. The system follows this loop and collects successive position and time data (trackpoints) of the person during the person's exercise event.

If the person requests an interim progress display at step 218 or indicates that the exercise event is complete at step 220, the system then proceeds to the energy expenditure analysis at step 224. Alternatively, the energy expenditure analysis can be preformed after each location capture. Accordingly, the system proceeds to steps 224 after each location capture, even if the user does not prompt an interim display at step 218 or indicate an end condition at step 220.

At step 226, the system determines the change in horizontal distance between successive trackpoints along the route. This is accomplished by calculating the difference of position coordinates (latitude and longitude) between a first position and a previous, second position. That difference represents the horizontal distance traveled by the user between successive trackpoints. This process is repeated for all the successive trackpoints and all the positioning deltas can be totaled to arrive at the total horizontal distance traveled by the person during the exercise event. This represents the horizontal distance traveled by the person along the route. For example, the horizontal distance between two trackpoints (a current trackpoint and a previous trackpoint) can be calculated using the spherical law of cosines using the formula:

Distance[horizontal]=acos(sin(Previous latitude)*sin(Current latitude)+cos(Previous latitude)*cos(Current latitude)*cos(Current longitude−Previous longitude))*6371000.

The spherical law of cosines is accurate to about 0.3%—which is likely to be sufficient given the overall GPS inaccuracy. However, there also exist more precise, numerically stable calculations based on a proper WGS84 ellipsoid, which can be used in other arrangements.

At step 228, the delta time is calculated by taking the difference in the times between two trackpoints. The total time of the exercise event can be calculated by aggregating all the delta times between all of the successive track points. At step 230, the average velocity of the person between two trackpoints can be calculated by dividing the delta distance by the delta time between the trackpoints.

At step 232, the position information for one or all of the trackpoints is transmitted to a remote server 104 using the mobile electronic device 102 communication interface 110. The remote server 104 includes a database that includes topographic data (i.e., data that includes elevation for particular geographic points). The remote server 104 receives the position data from the mobile electronic device 102 and then correlates that position data to the topographic data in order to determine the elevation that corresponds to that position. Thus, the system relies on topographic map data to determine elevation at a trackpoint as opposed to using GPS to determine elevation. The present system offers significant advantages over systems that rely on GPS calculation to determine elevation because such GPS systems have higher levels of inaccuracies.

The present system uses position coordinates and then uses topographic map data (e.g., United States Geological Survey data), which typically has a high degree of accuracy, in order to determine the elevation of the person at a particular position. The elevation at the position coordinate of a trackpoint can be calculated a number of different ways using a number of different methods. One method of calculating the elevation corresponding to a trackpoint relies on digital elevation model data in which elevation information is provided only at specific grid positions. Accordingly, if the position of a trackpoint (latitude and longitude) does not correspond to an existing grid position, the elevation must be calculated using neighboring grid positions and interpolating to determining the elevation at the trackpoint. The elevation (height) of a particular trackpoint can be calculated using variables and equations, as follows:

| Variable | Description |
| --- | --- |
| Size[grid] | Size of the grid, i.e. distance between neighboring grid lines |
| lat, lng | Latitude and longitude of trackpoint |
| n, s, e, w | Grid lines positions (latitude and longitude) that neighbor the trackpoint (north, south, east, and west of the trackpoint) |
| Weight[n], Weight[s], Weight[e], Weight[w] | Weight of neighboring grid lines |
| Weight[ne], Weight[nw], Weight[se], Weight[sw] | Weight of neighboring grid corners |
| Height[ne], Height[nw], Height[se], Height[sw] | Height of neighboring grid corner according to digital elevation model |
| Height | Interpolated height |

The weight of the four grid lines neighboring the position of the trackpoint can be calculated as follows:

$$Weight[n]=1-(n-lat)/Size[grid]$$

$$Weight[s]=1-(lat-s)/Size[grid]$$

$$Weight[e]=1-(e-lng)/Size[grid]$$

$$Weight[w]=1-(lng-w)/Size[grid]$$

The weight of the four grid corners neighboring the position of the trackpoint can be calculated as follows:

$$Weight[ne]=Weight[n]*Weight[e]$$

$$Weight[nw]=Weight[n]*Weight[w]$$

$$Weight[se]=Weight[s]*Weight[e]$$

$$Weight[sw]=Weight[s]*Weight[w]$$

The interpolated height of the trackpoint can be calculated as follows:

$$Height=(Height[ne]*Weight[ne]+Height[nw]*Weight[nw]+Height[se]*Weight[se]+Height[sw]*Weight[sw])/(Weight[ne]+Weight[nw]+Weight[se]+Weight[sw])$$

Accordingly, the height (elevation) of each trackpoint can be calculated using digital elevation models of the terrain corresponding to the trackpoints along the exercise route of the person.

The mobile electronic device 102 then receives the elevation values from the remote server 204 via its communication interface 110 at step 234. This process is repeated for each trackpoint captured along the route.

As shown in FIG. 2, the steps of transmitting position(s) 232 and receiving elevation values corresponding to the position(s) 234 are performed during the energy expenditure analysis process 224, which is triggered when the user requests an interim progress display at step 218 or indicates the exercise event is ended at step 220. However, transmitting (232) to the server and receiving the elevation values (234) after the server calculates the values for all the stored trackpoints can be a time consuming process. Accordingly, as shown in dashed lines, steps 232 and 234 can alternatively be performed after each position capture step 214. Accordingly, the system transmits the positions and receives elevations as the position information is captured. Thus, when the user prompts a progress display or indicates the exercise event is complete, the system relies upon the already stored elevation data, which can reduce the time to calculate the energy expenditure.

At step 236, the delta elevation or change in vertical distance between successive trackpoints is calculated.

At step 238, the effective distance traveled by the person is calculated using the delta distance (horizontal) data and the delta elevation (vertical) data calculated at steps 226 and 236, respectively. The effective distance can be calculated using the formula:

$$Effective\ Distance=sqrt((delta\ distance)^2+(delta\ elevation)^2).$$

The energy expenditure of the person between trackpoints is calculated at step 240 using an algorithm, the profile data (202/208), the event detail data (210), and the calculated effective distance (238) of the exercise route. The algorithm that is used to calculate the energy expenditure can be dependent on the type of activity performed by the person. For example, the characteristics of biking require that different factors be taken into account to determine the energy expended. Biking generally involves greater speeds which makes the wind velocity and air resistance relevant (e.g., riding against a strong wind requires more work). Biking also requires taking into account the rolling friction of the tire, which is dependent on the type of tire and the tire pressure. When biking, a rider can coast on the down hills which requires less work from the rider, whereas coasting is not possible while running. An exemplary algorithm and variables for determining energy expenditure during biking are provided as follows:

| Variable | Description |
| --- | --- |
| F | Force to overcome by the biker, in Newton |
| W | Weight of the biker and the bike, in kilograms |
| V | Velocity of the biker, relative to the ground, in meters per second |
| V[wind] | Wind velocity, adverse, in meters per second |
| C[friction] | Rolling friction coefficient, depending on tyre, tyre pressure, ground |
| C[air] | Air resistance coefficient, depending on bike form, body posture, biker clothing |
| G | Graviational acceleration of the earth, in meters per second^2 |
| Pct[slope] | Slope percentage, defined as Distance[vertical]/Distance[horizontal] |
| E | Expended energy of the biker, in Joule |
| D | Distance traveled by the biker, in meters |
| C[biker] | Biker energy transfer coefficient, depending on the physiological characteristics of the biker |
| T | Time spent biking, in seconds |
| P[exp] | Expended power of the biker, in Watt |
| P[eff] | Effective power of the biker, in Watt |

The force (F) can be calculated as follows:

$$F=C[friction]*W*cos(arctan(Pct[slope]))+C[air]*(V+V[wind])^2+G*W*sin(arctan(Pct[slope]))$$

Using the force (F), calculated above, the energy expended (E) by the biker can be calculated as follows:

$$E=F*D*C[biker]$$

The expended power (P[exp]) of the biker can be calculated as follows:

$$P[exp]=E/T=F*D*C[biker]/T=F*V*C[biker]$$

The effective power (P[eff]) of the biker can be calculated as follows:

$$P[eff]=F*V$$

An example calculation of a biker that weighs 90 kg, going up a 5% slope for 1 kilometer at a velocity of 12 km/h, using a hybrid bike with a well inflated tire on a clean, paved road, is provided as follows:

| Variable | Value |
| --- | --- |
| W | 90 kg |
| V | 3.3 m/s |
| V[wind] | 0 m/s |
| C[friction] | 0.1 |
| C[air] | 0.45 |
| Pct[slope] | 0.05 |
| G | 9.81 m/s^2 |
| D | 1000 m |
| C[biker] | 4.0 |

The calculations are as follows:

$$F=9.0+4.9+44.1=58 \text{ [Netwon]}$$

$$E=58*1000*4=232000 \text{ [Joule]}=55.4 \text{ [kcal]}$$

$$\text{[exp]}=765 \text{ [Watt]}$$

$$P\text{[eff]}=191 \text{ [Watt]}$$

As discussed above, because of the different characteristics of certain exercise activities, different algorithms can be used to more accurately calculate the energy expended by a person during an activity. In addition, different algorithms can be used depending on whether the person is moving uphill or downhill along the route. For example, a different algorithm can be used if the person is biking downhill because coasting becomes a factor in the determination. A person that is coasting exerts less energy than a person that is pedaling uphill over a certain distance. According, the energy expenditure result for downhill sections can be reduced by a weighting factor (e.g., reduced by (50%) for downhill sections. Alternatively, the terminal velocity for a give slope, taking into account friction, wind resistance, etc., can be calculated assuming no pedaling from the rider (i.e., 100% coasting). Then, the actual velocity at the end of the slope can be measured. If the measured actual velocity is greater than the calculated terminal velocity (meaning that the rider had to contribute energy to account for the increased speed), the amount of energy required to achieve the excess velocity can be calculated.

As an example of another algorithm that can be used for a different activity, one method of determining the energy expenditure during running or walking is based on the oxygen consumption of the runner/walker. An exemplary algorithm and variables for determining energy expenditure during running/walking are provided as follows:

| Variable | Description |
| --- | --- |
| VO2 | Oxygen consumption |
| C[horizontal] | Oxygen consumption coefficient for horizontal movement |
| C[vertical] | Oxygen consumption coefficient for vertical movement |
| Pct[slope] | Slope percentage |
| E | Energy expended by the runner |
| W | Weight of the runner |
| D | Distance run by the runner |
| P[exp] | Power expended by the runner |
| T | Time spent running |
| V | Velocity of the runner |
| C[runner] | Energy transfer coefficient of the runner |

The oxygen consumption (VO2) can be calculated as follows:

$$VO2=C\text{[horizontal]}+C\text{[vertical]}*Pct\text{[slope]}$$

Using the oxygen consumption (VO2), calculated above, the energy expended (E) by the runner/walker can be calculated as follows:

$$E=VO2*W*D*C\text{[runner]}$$

The expended power (P[exp]) of the runner/walker can be calculated as follows:

$$P\text{[exp]}=E/T=VO2*W*D*C\text{[runner]}/T=VO2*W*V*C\text{[runner]}$$

An example calculation of a runner that weighs 82 kg, going up a 5% slope for 1 kilometer at a velocity of 8 km/h, on a clean, paved road, is provided as follows:

| Variable | Value |
| --- | --- |
| W | 82 kg |
| V | 2.2 m/s |
| D | 1000 m |
| C[horizontal] | 0.2 mL/(kg * m) |
| C[vertical] | 0.9 mL/(kg * m) |
| C[runner] | 21.1383 J/mL |

The calculations are as follows:

$$VO2=0.2+0.9*0.045=0.2405 \text{ [mL/(kg*m)]}$$

$$E=0.2405*82*1000*21.1383=416868 \text{ [J]}=99.6 \text{ [kcal]}$$

$$\text{[exp]}=917 \text{ [Watt]}$$

These are just two examples of algorithms and factors that can be used to determine energy expenditure during a given exercise. Other variables, such as ambient temperature, can also be included in the calculations. They can be included as separate variables in the calculation and/or they can be included as weighting factors. For example, exercising in hot weather is results in greater energy expenditure. Thus, for every degree above an ideal temperature, the calculated energy expended can be increased by multiplying it by a weighting factor. For example, for every degree Fahrenheit over 60 degrees, the energy expended value can be increase by 1% by multiplying it by a weighting factor.

The energy expended during this exercise event is then added to the person's profile at step 242. This energy expenditure information can also be used to calculate an overall health score of the person, as described more fully in copending provisional patent application Ser. No. 61/387,906, filed on Sep. 29, 2010, and titled HEALTH DATA ACQUISITION, PROCESSING AND COMMUNICATION SYSTEM. The updated health score of the person can also be published to a social networking site, as described in the 61/387,906 application, so that others may view the health score and/or the exercise activity of the person.

At step 244, the statistics of the exercise event can be sent to the graphic user interface and displayed on the display 114 of the mobile electronic device 102. The statistics may include total distance traveled, total elevation change, total time, average velocity, and energy expended.

The system ends at step 246 if the user indicated that the exercise event was over at step 220. If the user requested an interim progress display at step 218, and the exercise event is not yet complete, the system returns to step 214 to begin collection of additional trackpoints as the person continues the exercise event.

There are many possible variations to the steps described above in connection with FIG. 2. For example, as described above, the position data is transmitted to the remote server and the elevation corresponding to that position is received by the mobile device. Alternatively, the position data can be transmitted to the remote server and the mobile electronic device can receive the digital elevation model data with the grid points from the server. In this arrangement, the calculations for interpolating the height at the positions can be performed by the mobile device instead of the remote server. In another arrangement, the profile data, event detail data, position data, and time data can be transmitted to the remote server. The remote server can then perform all the calculations necessary to determine the energy expended by the person. Then the mobile device can receive the energy expended values from the server and display them without having to perform the calculations.

The system 100 can also be used to predict the energy that a person would expend if the person exercised along a particular route. The predictive function can be used by the user to determine which exercise route is best suited for the user's exercise objectives. For example, the user can use the mobile device 102 to retrieve map data from the internet 118. The users can then set a start point and an end point on the map and the device can present several different possible exercise routes between the start and end points. The different routes can have different distances, difference elevation changes, and different terrain conditions. This information can be contained in the map data retrieved from the internet. The user can then indicate the type of exercise (e.g., biking, running, etc.) the person intends to engage in and the intended speed of the exercise. The system then divides the proposed routes into a number of position trackpoints. The position trackpoints are then transmitted to the remote server. The remove server calculates the corresponding elevation information, as discussed above, and the device receives the elevation information from the server. The device then calculates, as discussed above, the predicted energy that would be expended for the selected activity along each proposed route. Thus, if a person has a goal to expend a certain amount of energy (e.g., burn 1000 calories), the person can select a route that is predicted to achieve this goal.

Figure 3:
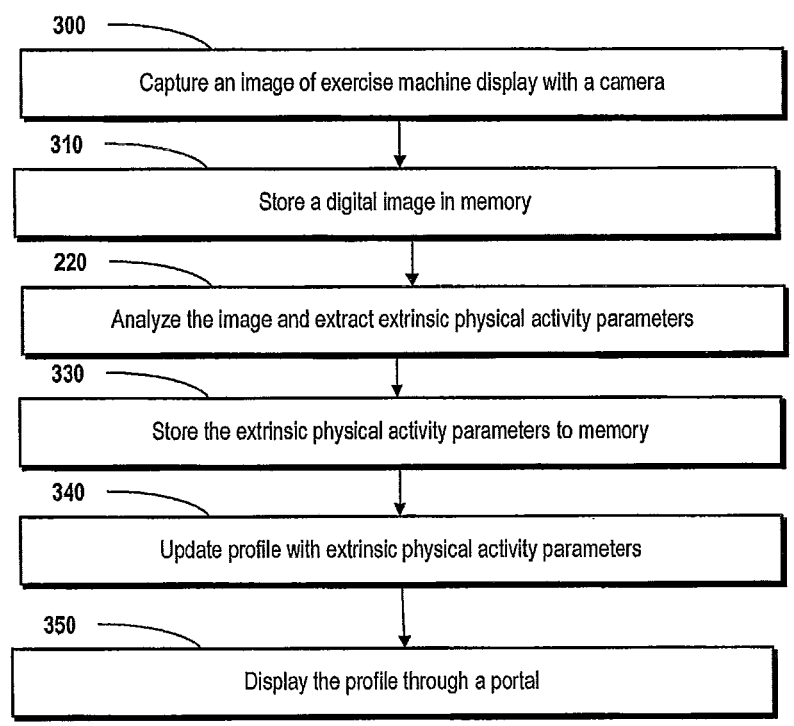
FIG. 3 is a flowchart illustrating a computer implemented method for managing health related data.

Referring now to FIG. 3, a flow diagram illustrates functionality suitable for managing health-related data captured from an exercise machine with a camera. The system 100 can be used by the person in order to capture extrinsic physical activity parameters from a display 111 of an exercise machine 107 and record that information to a personal log containing historical exercise activity information.

At step 300, a person captures an image that includes the display 111 of an exercise machine 107 using a mobile device 102 with a camera 117 or a different type of camera. The exercise machine 107 is not limited to a particular type of machine such as a treadmill, stationary bike, elliptical trainer, rowing machines, and the exercise machine 107 is not limited to a particular manufacturer or model.

At step 310 the processor 106, executing one or more software modules 109, is configured to store the digital image captured by the camera 117 in memory 108. The image can be stored locally on the mobile device 102 or remotely on another device such as a server 104. Similarly, further processing by the processor 106 on the image can be performed locally or remotely or a combination of remote and local processing.

At step 320 the processor 106, executing one or more software modules, 109 is configured to determine, from the image, the extrinsic physical activity parameters that were shown on the display 111 of the exercise machine 107.

In one arrangement, the extrinsic physical parameters can be determined by implementing an optical character recognition (OCR) algorithm. OCR algorithms, which are known in the art, are used to distinguish text characters from other image data (e.g. non-text like trees etc.) and record that information including the character and the associated location of the character in the image.

The processor 106 can be configured to implement an OCR algorithm to identify characters in the image data and associated location of the character and a confidence score which corresponds to how likely the algorithm was correct in identifying a particular character.

The processor 106 can also analyze the OCR data, including characters, locations, and confidence, using a sequencing algorithm. The sequencing algorithm, can analyze the OCR data to find characters that are in proximity and of the same type (i.e. letter or number) that should be grouped together. For example, the two numbers 1 and 0 next to two letters k and m can be grouped as independently as "10" and "km". By way of further example and not limitation, the grouping algorithm can also configure the processor to group numbers separated by a ":" together, for example 10:55 is grouped together as "10:55" instead of "10" ":" and "55". The sequencing algorithm sorts the raw OCR data into more meaningful sequenced data that can be further manipulated and analyzed by the processor 106.

The processor 106 can be configured to further categorize the sequenced data using a sorting algorithm. The sorting algorithm can compare the sequenced data to known types of information and categorize accordingly. Some categorizes include, numbers, such as "112" or "198.8", durations, such as numbers grouped together separated by a ":" or units such as groups of letters and symbols such as "kcal" or "km/h". Similarly, the processor 106 can further categorize units into their specific types including as "energy" or "time" or "distance" by comparing the unit to a list of known units and types that are stored in memory 108.

The processor 106 executing one or more software modules 109 can determine if sequences of characters that are categorized as a number or duration are associated with a particular unit by comparing the location of the number or duration to the location of the unit. For example, if the location of a unit is intersected by whole or in part by the location of a number or duration, either vertically or horizontally, the unit and the number or duration can be associated. The amount by which a unit and a number or duration need to intersect in order to be associated with one another can be a predetermined percentage, for example 80%.

If there are multiple numbers and/or durations that intersect with a unit, the processor can be configured to associate the unit to the number or duration that is in closest proximity to the unit. If one or more durations are identified, however, there is no unit that is categorized as "time" associated with the one or more durations, the processor 106 executing one or more software modules 109 is configured to analyze the area of the one or more durations and determine the largest duration in terms of area. The processor can be configured to associate the largest duration, in terms of area, to the elapsed work-out time.

In another arrangement, the processor 106 executing one or more software modules 109 is configured to extract extrinsic physical activity parameters from an image captured by the camera 102 can also incorporate the step of first identifying the make (manufacturer brand) and model exercise machine 107 that was being used by the person. The processor 106 can be configured to implement a photo comparison algorithm to compare the image to a database of photos of known exercise machines which is stored in memory 108. Photo comparison algorithms are known in the art and work by comparing the features of one image to another to determine the degree of similarity. If the image corresponds to a photo of a known exercise machine, within a pre-determined degree of confidence, the processor can analyze the image for extrinsic physical activity parameters according to a specific algorithm tailored to that exercise machine.

If the image does not correspond to a photo of a known exercise machine within the pre-determined degree of confidence, the processor 106 can be configured to prompt the user to confirm the make and model of the exercise machine or manually input the manufacturer and model using the interface 115, or prompt the user to re-capture the image with the camera and try again.

Determining the make and model of the exercise machine prior to analyzing the text information in the image can help reduce the amount of image data that the processor 106 needs to analyze. By example, if it is known that a Precor™ treadmill displays the distance traveled during the workout in the upper right hand corner of the screen, and amount of calories burned in the bottom right, the system need only analyze the upper right portion of the image to locate and extract the information that corresponds to distance traveled and the bottom right for calories burned.

At step 330, the extrinsic physical activity parameters are stored into memory 108.

At step 340, the extrinsic physical activity parameters can then be added to the person's profile. The profile, as discussed above, contains physiological and other health and exercise related information about the person, and is a continuous log of extrinsic physical activity parameters corresponding to past work-out sessions that allows the user to track their activity and progress and overall health.

At step 360, the profile can be provided to the user through a portal. The portal can include, but is not limited to, an application on the person's mobile device or a web-based portal accessible through the internet.

The extrinsic physical activity parameters can also be used to calculate an overall health score of the person, as described more fully in below and in: Provisional patent application Ser. No. 61/387,906, filed on Sep. 29, 2010, and WO Patent Application No. PCT/US11/53971 filed on Sep. 29, 2011 titled HEALTH DATA ACQUISITION, PROCESSING AND COMMUNICATION SYSTEM, the entireties of which are hereby incorporated by reference. The updated health score of the person can also be published to a social networking site, as described in the 61/387,906 application, so that others may view the health score and/or the exercise activity of the person.

In another implementation, referring to FIGS. 4-7, a system 1100 includes a computer-based application for the collection of health related parameters of a user and a user interface 1110 for the display of data. The computer-based application is implemented via a microcontroller 1120 that includes a processor 1124, a memory 1122 and code executing therein so as to configure the processor to perform the functionality described herein. The memory is for storing data and instructions suitable for controlling the operation of the processor. An implementation of memory can include, by way of example and not limitation, a random access memory (RAM), a hard drive, or a read only memory (ROM). One of the components stored in the memory is a program. The program includes instructions that cause the processor to execute steps that implement the methods described herein. The program can be implemented as a single module or as a plurality of modules that operate in cooperation with one another. The program is contemplated as representing a software component that can be used in connection with an embodiment of the invention.

A communication subsystem 1125 is provided for communicating information from the microprocessor 1120 to the user interface 1110, such as an external device (e.g., handheld unit or a computer that is connected over a network to the communication subsystem 1125). Information can be communicated by the communication subsystem 1125 in a variety of ways including Bluetooth, WiFi, WiMax, RF transmission, and so on. A number of different network topologies can be utilized in a conventional manner, such as wired, optical, 3G, 4G networks, and so on.

The communication subsystem can be part of a communicative electronic device including, by way of example, a smart phone or cellular telephone, a personal digital assistant (PDA), netbook, laptop computer, and so on. For instance, the communication subsystem 1125 can be directly connected through a device such as a smartphone such as an iPhone, Google Android Phone, BlackBerry, Microsoft Windows Mobile enabled phone, and so on, or a device such as a heart rate or blood pressure monitor (such as those manufactured by Withings SAS), weight measurement scales (such as those manufactured by Withings SAS), exercise equipment or the like. In each instance, the devices each comprise or interface with a module or unit for communication with the subsystem 1125 to allow information and control signals to flow between the subsystem 1125 and the external user interface device 1110. In short, the communication sub-system can cooperate with a conventional communicative device, or can be part of a device that is dedicated to the purpose of communicating information processed by the microcontroller 1120.

When a communicative electronic device such as the types noted above are used as an external user interface device 1110, the display, processor, and memory of such devices can be used to process the health related information in order to provide a numerical assessment. Otherwise, the system 1100 can include a display 1140 and a memory 1150 that are associated with the external device and used to support data communication in real-time or otherwise. More generally, the system 1100 includes a user interface which can be implemented, in part, by software modules executing in the processor of the microcontroller 1120 or under control of the external device 1130. In part, the user interface can also include an output device such as a display (e.g., the display 1140).

Biosensors 1115 can be used to directly collect health information about a user and report that information. The biosensor can be placed in contact with the user's body to measure vital signs or other health related information from the user. For example, the biosensor can be a pulse meter that is worn by the user in contact with the user's body so that the pulse of the user can be sensed, a heart rate monitor, an electrocardiogram device, a pedometer, a blood glucose monitor or one of many other devices or systems. The biosensor can include a communication module (e.g., communication subsystem 1125) so that the biosensor can communicate, either wired or wirelessly, the sensed data. The biosensor can communicate the sensed data to the user interface device, which in turn communicates that information to the microcontroller. Optionally, the biosensor can directly communicate the sensed the data to the microprocessor. The use of biosensors provides a degree of reliability in the data reported because it eliminates user error associated with manually, self-reported data.

Figure 4:
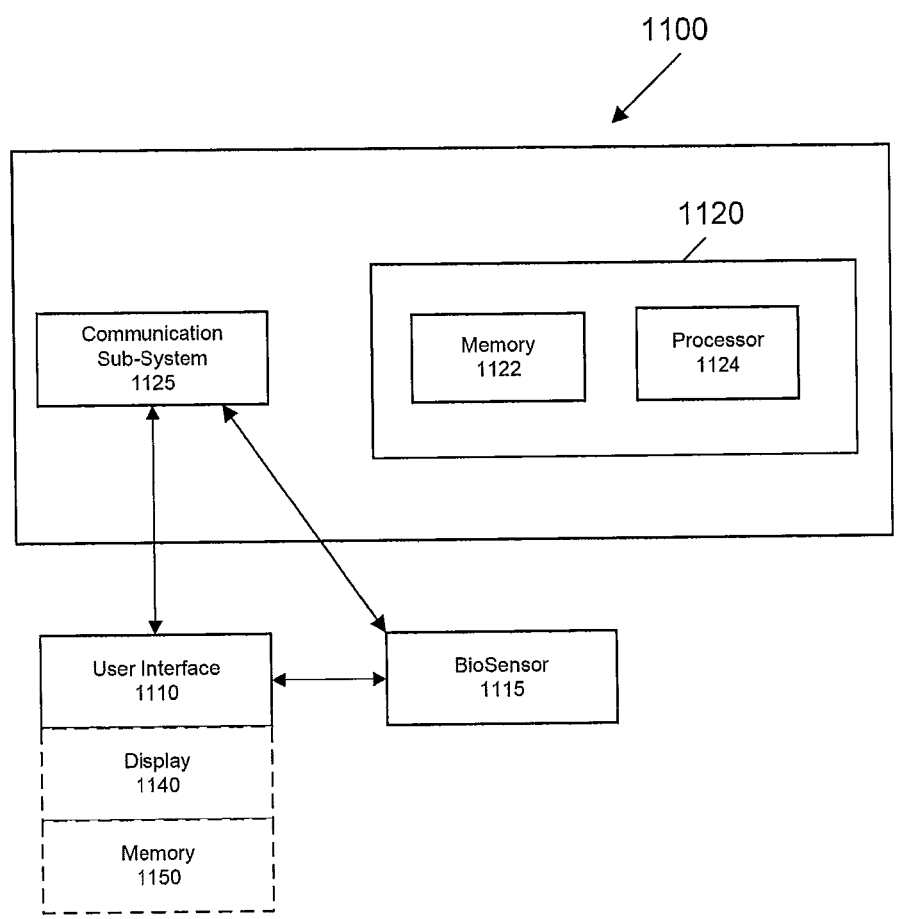
FIG. 4 is a schematic block diagram of a local health information collection and communication system according to a first implementation of the invention.
Figure 4A:
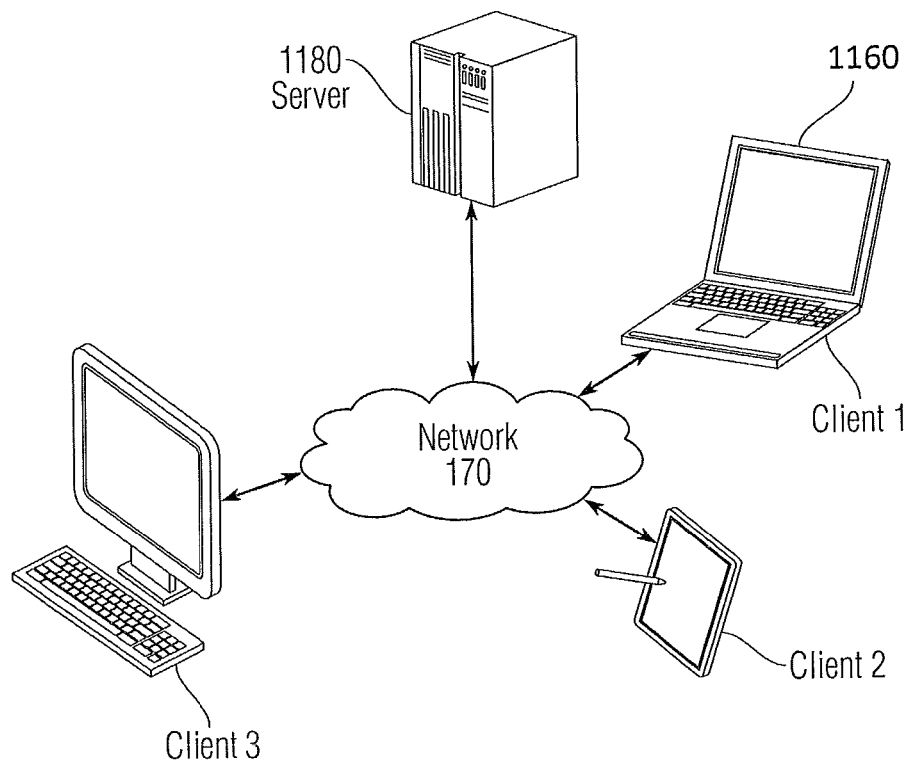
FIG. 4A is a network diagram according to another implementation of the invention.

Alternatively or in addition, the user can self-report his or her health related information by manually inputting the data. Thus, in another implementation, as shown in FIG. 4A, health related data of a person is entered directly into a computer 1160 and provided across a network 1170 to a server computer 1180. (All computers described herein have at least one processor and a memory.)

Regardless of the implementation, the system provides a means for assigning a numerical value that represents the relative health of an individual. The numerical value is described herein as a "health score" and can be used to assess to the individual's health based on health related information collected from a user. The health score is calculated based on the collected health information using an algorithm. The user or the communication subsystem 1125 provides the system the health related information concerning a number of health parameters. Predetermined weighting factors are used to assign a relative value of each of the parameters that are used to calculate the health score. The user's health score is then calculated by combining the weighted parameters in accordance with an algorithm. For example, the parameters can be a person's blood glucose level and body weight. A weighting factor "a" is applied to the blood glucose data and a weight factor "b" can be applied to the body weight data. If the blood glucose data is a more important factor in determining a person's health than body weight, then the weighting factor "a" will be larger than weighting factor "b" so that the blood glucose data has a larger impact on the calculated health score (e.g., Healthscore=Glucose*a+(Weight/100)*b). In certain implementations, the weighting factor is a non-unity value (e.g., greater or less than one, but not one). Fewer or additional factors can be included in the calculation of the health score, and an offset value can be included that is added or subtracted or which modifies the entire calculation, in certain implementations such as to account for age or gender as two possible reasons; however, the foregoing is intended as a non-limiting example of how to calculate a health score. Other parameters that can be measured and included in the calculation include blood pressure measurements, height, body mass index, fat mass, medical conditions such as diabetes, ventricular hypertrophy, hypertension, irregular heartbeat and fasting glucose values. Where absent, a parameter can be omitted from the calculation or it can be estimated from other parameters and/or values obtained from a sample group of individuals having similar parameters.

In addition to intrinsic medical parameters, physical activity of a user is also taken into account when calculating his or her health score. Physical activity can be monitored via an appropriate sensor dependent on the activity. Sensors can include a GPS unit, an altimeter, a depth meter, a pedometer, a cadence sensor, a velocity sensor, a heart rate monitor or the like. In the case of gym-based activities, computerized exercise equipment can be configured to provide data directly on the program completed by the user (for example, a so-called elliptical/cross-trainer can provide far better data on the workout than a user's pedometer etc). Although automated capture of parameters concerning a user's physical activity is preferred, a user interface for manual activity entry is also provided. In this regard, an exercise machine such as a treadmill, elliptical, stationary bike or weight lifting machine with a rack of weights or bands can be provided with a communications interface to communicate with the system described herein to provide extrinsic physical activity parameters to the system and to receive and further include a processor configured to process data from the system so as to automatically adjust an exercise program at the exercise machine to meet a goal, challenge, or other objective for that user.

Lifestyle data such as diet, smoking, alcohol consumed and the like can also be collected and used in calculating the health score. In one embodiment, a barcode or RFID scanner can be used by a user to capture data on consumed foodstuffs that is then translated at a remote system, such as the server 1180 or a website in communication with the server 1180, into parameters such as daily calorie, fat and salt intake. In part, the system relies on such data being provided by the user while other data can be obtained through data network connections once permissions and connectivity rights are in place.

Physical activity and lifestyle data is tracked over time and a decay algorithm is applied when calculating its effect on the health score, as is discussed in more detail below. As such, physical activity far in the past has a reduced positive effect on the health score. Preferably, the weighting factors used in the algorithm for the computation of the health score are adjusted over time in accordance with a decay component which is arranged to reduce the relative weight of the parameters that are used in the calculation. The decay component can itself comprise a weighting value, but can also comprise an equation that takes into account at least one factor associated specifically with the user, such as the user's weight or weight range, age or age range, any medical conditions known to the system, and any of the other parameters that may be known to the system, or a curve that is configured in view of these factors so that a value can be read from the curve as a function of the values along the axes for that user. In this way, the decay component can reduce the relative weight of the parameters used in the health score calculation for a first user differently than for another user, such as when the first user has a first age or age range and the second user has a second age or age range.

A central system, preferably a database and website that can be hosted, for example, by the server 1180, maintains data on each user and his or her health score and associated parameters and their trends over time. The data can be maintained in such a way that sensitive data is stored independent of human identities, as understood in the art.

The calculated health score for each user is then processed in dependence on a system, group or user profile at the central system. Depending on the profile settings, the health score and trends associated can cause various automated actions. For example, it can cause: triggering of an automated alert; providing user feedback such as a daily email update; triggering the communication of automated motivation, warnings and/or goal setting selected to alleviate a perceived issue; adjustment of a training programme; or automated referral for medical analysis.

The user's health score is also provided to a designated group of recipients via a communication portal. The group of recipients can comprise selected, other, users of the system (e.g., friends and family) so that the health scores of the selected, other users can be compared against the health score of still others. In alternative arrangements, all users can see other user's scores, or the group of recipients can be defined as a specific health insurance provider so that price quotes can be provided to insure the individual. Other possibilities are within the scope the invention.

Figure 5:
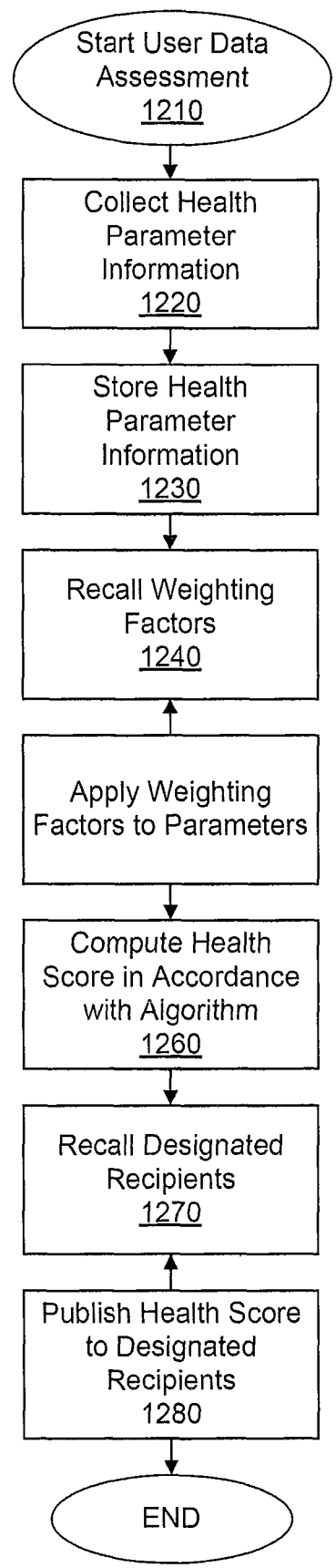
FIG. 5 is a schematic flow diagram according to one embodiment of the invention.

Referring now to FIG. 5, a schematic flow diagram according to one embodiment of the invention is described in support of an assessment of a person (e.g., a patient or user) to provide a health score. At step 1210, the user initiates the process for the collection, processing, and publishing of health related data. For example, a person using a mobile electronic device (e.g. a smart phone or portable computing device) selects the software application, which starts the program running on the device processor, or the user can access an Internet based web page in which code is executed on a remote processor and served to the user's local device. An identification module prompts the user to identify himself and authenticate his identity. This can be accomplished by prompting the user to enter a user name and password, or by other means, such as a fingerprint reader, keyfob, encryption or other mechanism to ensure that identity of the user. Alternatively, if the user is accessing the system via a personal electronic device, identification data can be stored in the local device memory and automatically accessed in order to automatically confirm the identity of the user.

At step 1220, a data collection module executing on the processor can prompt the user to provide health related data corresponding to a number of parameters. In one implementation, one or more the parameters are provided automatically by the communication subsystem 1125. The parameters can include the user's body weight, height, age and fitness activity information. Such measurable medical parameters are intrinsic parameters of the user. The user's body weight and height provide information about the user's current state of health. The fitness activity information corresponds to the amount of exercise the user engages in. This information is an example of a physically activity parameter that is an extrinsic parameter of the user. For example, the user can enter information about his or her daily fitness activities, such as the amount of time the user engaged in physical activity and the type of physical activity. If the user went to the gym and exercised on a bicycle for thirty minutes, for example, that information is entered into the system. The user's fitness activity information provides information about the actions that are being taken by the user in order to improve his or her fitness.

A user's body weight, height, age and fitness activity information are just some of the parameters for which information can be collected. The system can collect and process a multitude of other parameters that can be indicative of a user's health. For example, parameters can include blood glucose levels, blood pressure, blood chemistry data (e.g., hormone levels, essential vitamin and mineral levels, etc.), cholesterol levels, immunization data, pulse, blood oxygen content, information concerning food consumed (e.g., calorie, fat, fiber, sodium content), body temperature, which are just some of a few possible, non-limiting examples of parameters that can be collected. Various other parameters that are indicative of a person's health that can be reliably measured could be used to calculate a person's health score.

The collected health parameter information is stored in a memory at step 1230. At step 1240, a weighting module recalls weighting factors from the memory. The weighting factors can be multiplication coefficients that are used to increase or decrease the relative value of each health parameters. A weighting factor is assigned to each health parameter as shown in the formulas herein. The weighting factors are used to control the relative values of the health parameters. Some health parameters are more important than others in the calculation of the users health score. Accordingly, weighting factors are applied to the health parameters increase or decrease the relative affect each factor has in the calculation of the user's health score. For example, a user's current body weight can be more important than the amount of fitness activity the user engages in. In this example, the body weight parameter would be weighted more heavily by assigning a larger weighting factor to this parameter. At step 1205, the weighting module applies the recalled weighting factors to the collected health parameter values to provide weighted health parameter values. The weighting factor can be zero in which case a particular parameter has no impact on the health score. The weighting factor can be a negative value for use in some algorithms.

After the parameters have been weighted, the user's health score is computed at step 1260 via a scoring module operating in the processor. The scoring module combines the weighted parameters according to an algorithm. In one implementation, the health score is the average of the user's body mass index (BMI) health score and the user's fitness health score minus two times the number of years a person is younger than 95. The algorithm formula for this example is reproduced below:

$$\text{Health Score} = ((\text{BMI Healthscore} + \text{Fitness Healthscore})/2) - 2*(95-\text{Age}).$$

The user's BMI Healthscore is a value between 0 and 1000. The BMI Healthscore is based on the user's BMI, which is calculated based on the user's weight and height, and how much the user's BMI deviates from what is considered a healthy BMI. A chart or formula can be used to normalize the user's BMI information so that dissimilar information can be combined. A target BMI value is selected which is assigned a maximum point value (e.g. 1000). The more the user's BMI deviates from the target value the fewer points are awarded. The user's Fitness Healthscore is based on the physical activity or exercise of a person. In one embodiment, it is the sum of the number of fitness hours (i.e., the amount of time the user engaged in fitness activities) in the past 365 days where each hour is linearly aged over that time so that less recent activity is valued less. The resulting sum is multiplied by two and is capped at 1000. This normalized the fitness information so that it can be combined to arrive at the health score. A target daily average of fitness activity is selected and is awarded the maximum amount of points (e.g. 1000). The user is awarded fewer points based on how much less exercise that engage in compared to the target.

In another implementation, the health score is determined from a number of sub-scores that are maintained in parallel beyond the BMI health score and the fitness health score. Likewise, the health score can be determined using similar information in a combinative algorithm as discussed above using different or no age adjustments.

Figure 6A:
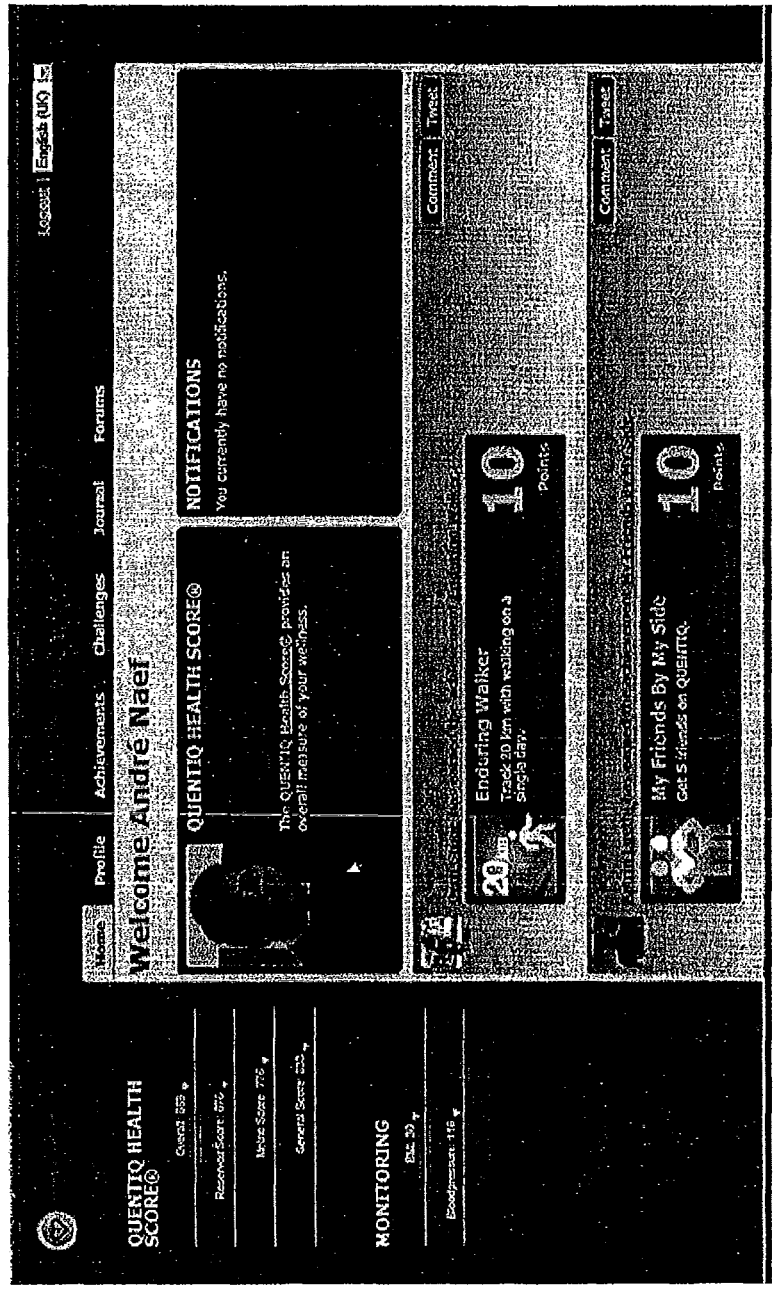
Figure 6B:
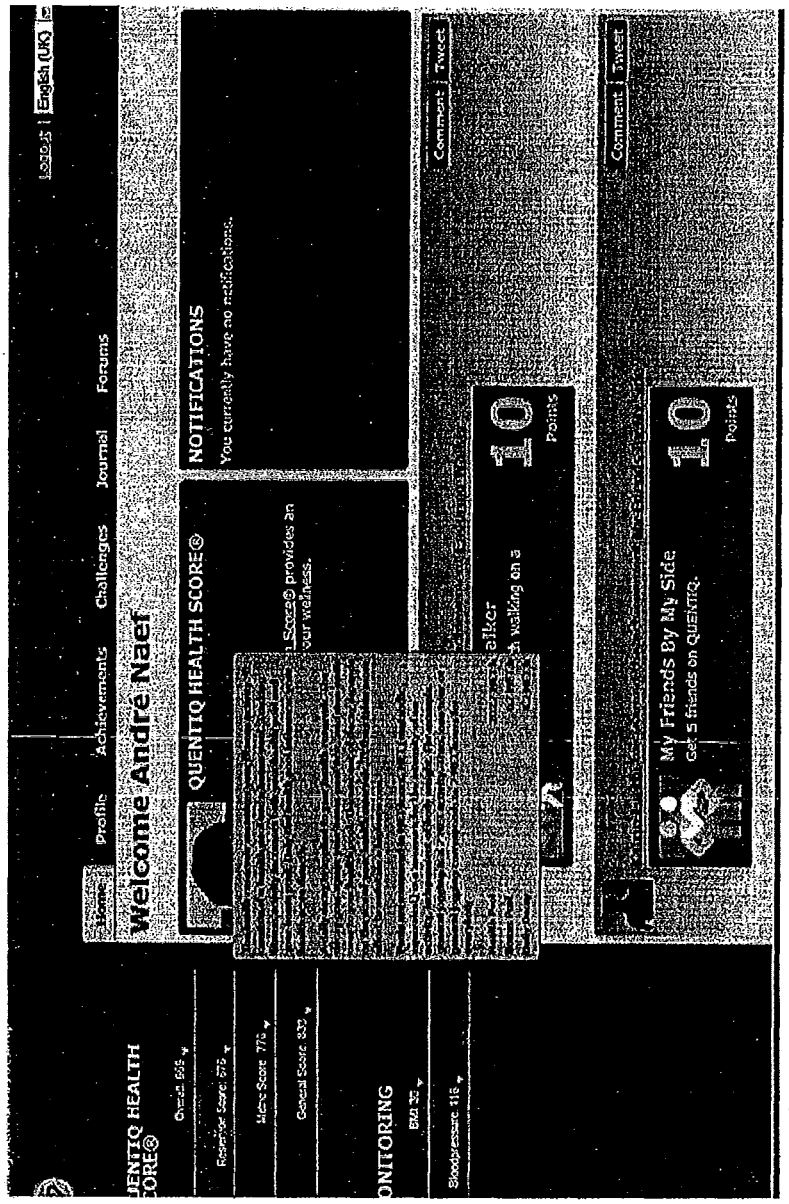
Figure 6C:
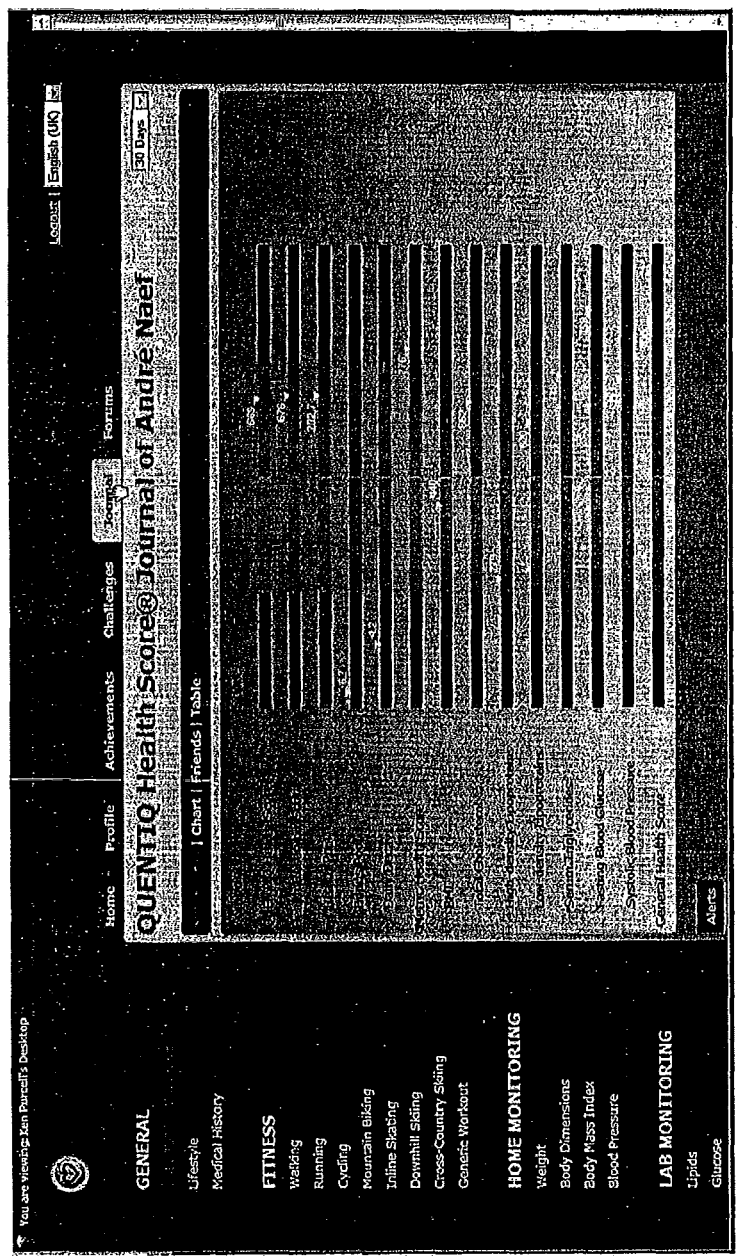

Intrinsic medical parameters are processed to determine a base health score. Extrinsic parameters such as those from physical exercise are processed to determine a value that is allocated to a health pool and a bonus pool. The value, preferably expressed in MET hours, associated with a physical activity is added to both the health pool and the bonus pool. A daily decay factor is applied to the bonus pool. Any excess decay that cannot be accommodated by the bonus pool is then deducted from the health pool. The amount of decay is determined dependent on the size of the health pool and bonus pool such that a greater effort is required to maintain a high health and bonus pool. The health pool value is processed in combination with the score from the intrinsic medical parameters in order to calculate the overall health score value, This can be on a similar basis to the earlier described implementation or it can include different parameters and weighting factors. In one embodiment, the health pool value is a logarithm or other statistical function is applied to age the respective values over time such that only the most recent activity is counted as being fully effective to the health/bonus pool. An example user interface showing the health score, the health reservoir and selected other measured parameters (as it will be appreciated that many simply combine to make up the scores) is shown in FIGS. 6a and 6b. Various sub-scores and their trends are recorded, as is shown in FIG. 6c.

As will be appreciated, MET hours are kcal expended divided by kilograms of body weight, i.e. 100 kcal expended by a person of 50 kg is 2 MET h. This is "normalized energy", making the system fair for persons of all weights. With this method, pools can be the same size for each per person as energy is normalized for the person based on his or her body weight.

In one implementation, each person is assigned a health pool having a capacity of 300 MET h and a bonus pool having a capacity of 60 MET h.

When someone performs activity A, the pools are updated as follows:

$$H=\min(H+A*\text{alpha}, 300)$$

$$B32 \min(B+A*(1-\text{alpha}), 60)$$

Where H is the health pool score, B is the bonus pool score, A is the MET h value for the activity and alpha is a system wide contestant (selected between 0 and 1) that determines the proportion in which the activity contributes to the respective pools.

The activity is split between the health pool and the bonus pool. Any excess MET h activity going over the cap of any pool is discarded. A daily decay value D is applied to the pools as follows:
D=f(H,B)
B=B−D
If B<0:
 D=D+B
 B=0
If D<0:
 D=0

The decay is fully applied to the bonus pool, and if the bonus pool is empty, the remainder is applied to the health pool. In this embodiment, no pool ever goes below zero.

Figure 6D:
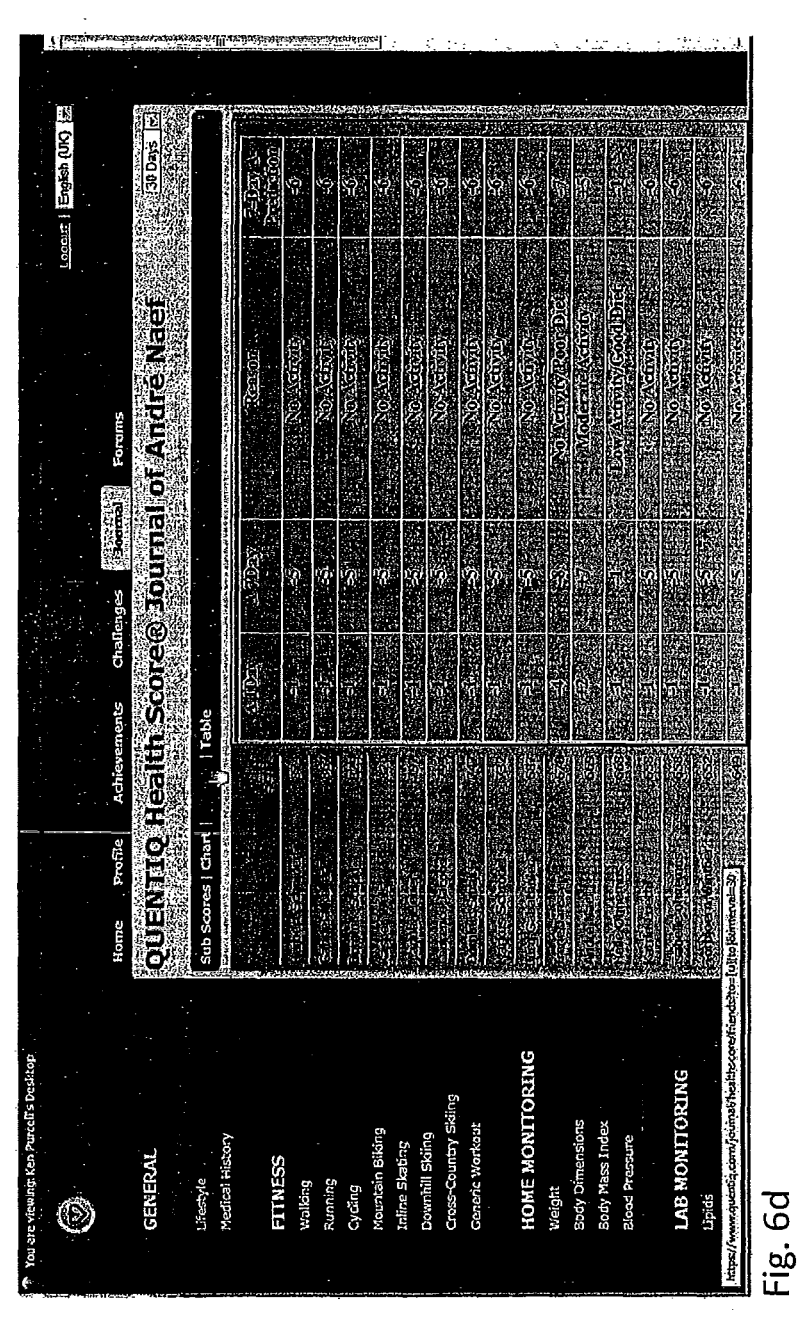
Figure 6E:
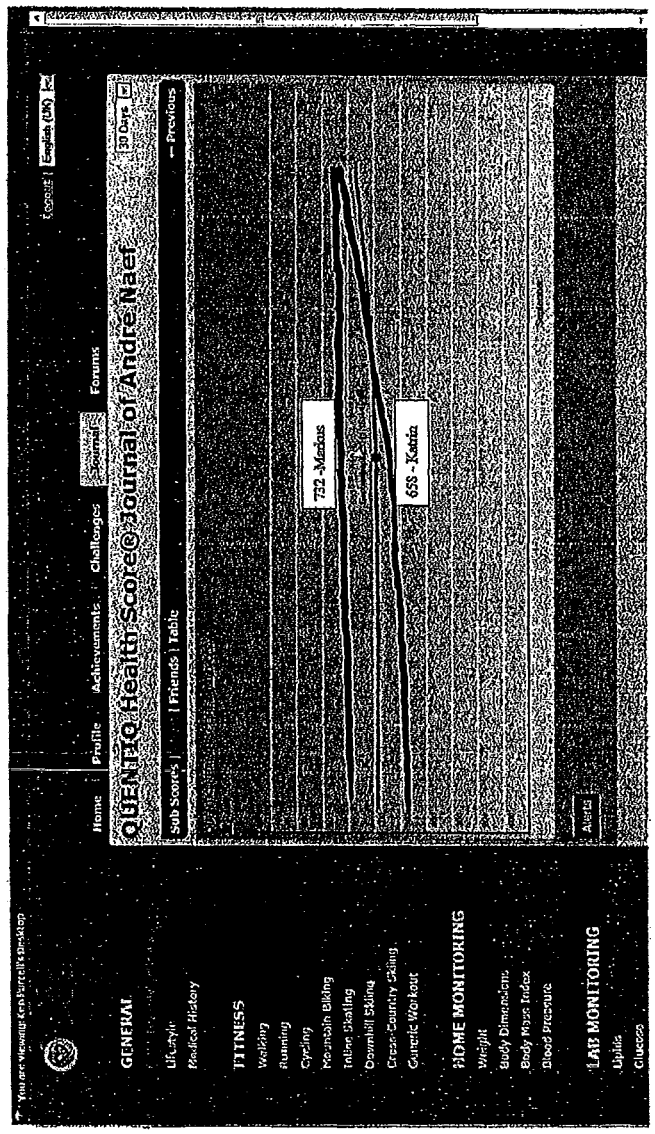
Figure 6F:
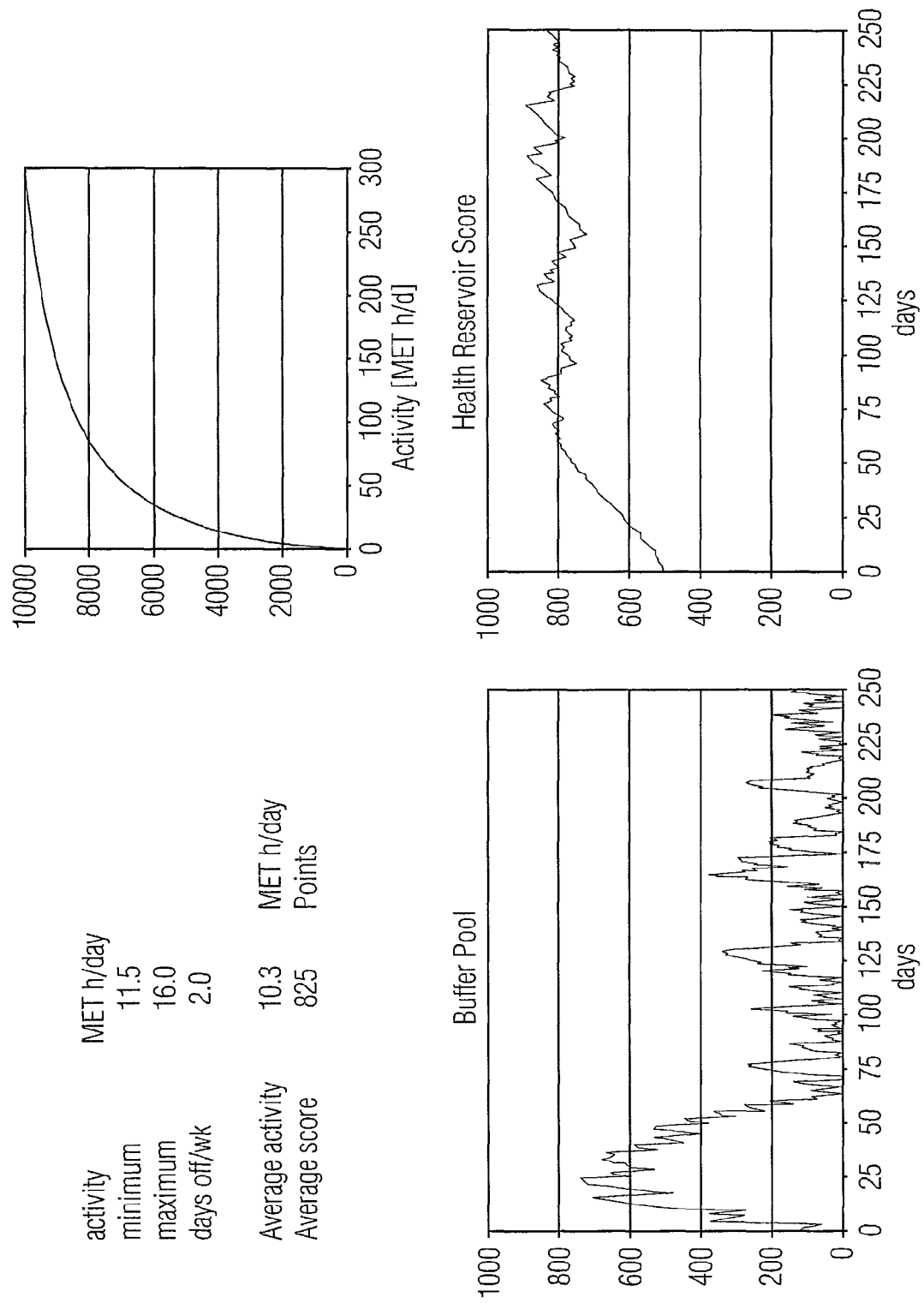
FIG. 6f is an illustration of progressions over time of parameters used to determine the health score in one embodiment of the invention.
Figure 7A:
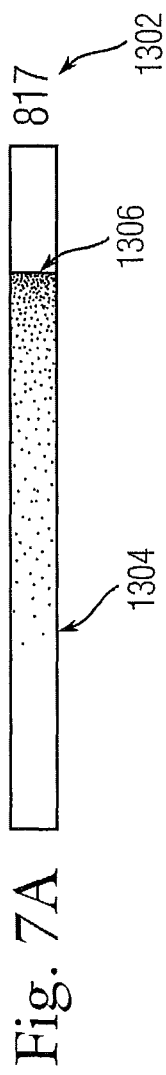
FIG. 7a is an illustration of a data presentation format according to one embodiment of the invention.
Figure 7B:
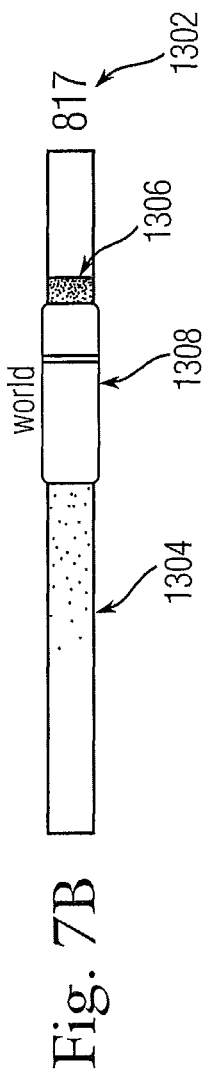
FIG. 7b is an illustration of a data presentation format according to one embodiment of the invention.
Figure 7C:
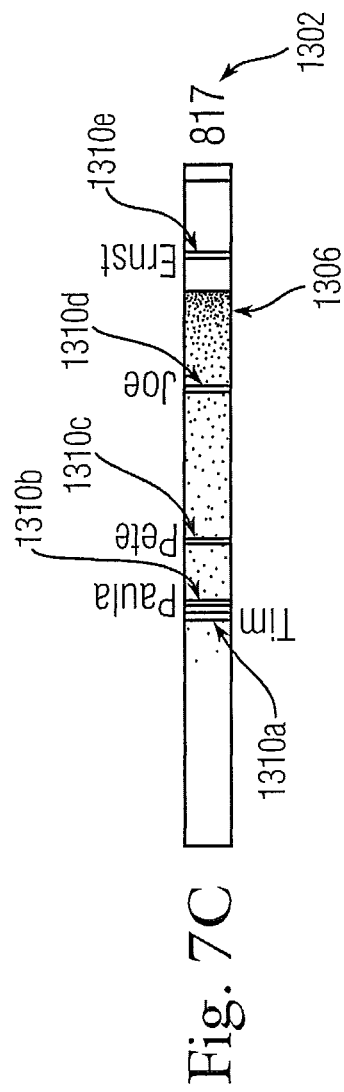
FIG. 7c is an illustration of a data presentation format according to one embodiment of the invention.
Figure 7D:
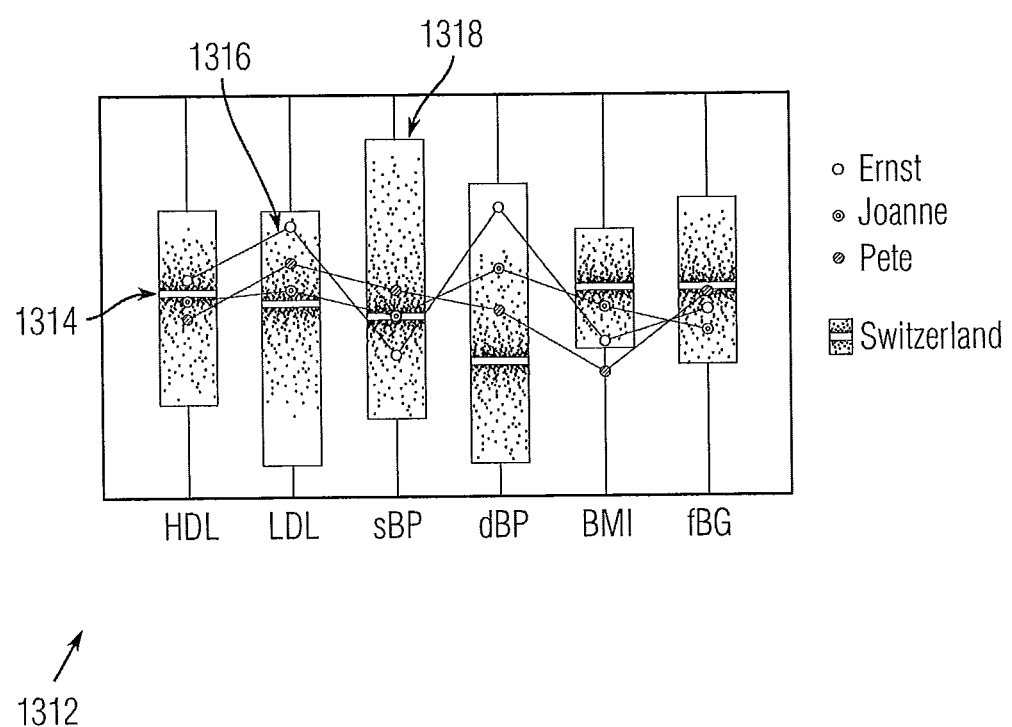
FIG. 7d is an illustration of a data presentation format according to one embodiment of the invention.

The system finds its equilibrium where A equals f(H, B), i.e. where the average daily activity matches the average daily decay. The function f(H, B) is highly non-linear with regard to H and B. In essence, it takes sub-linearly less effort to maintain a small pool, and super-linearly more effort to maintain a large pool. This is to make sure that the average person can maintain a, say, half-full health pool (150, corresponding to a score of 500), whereas it takes a massively higher effort (typically only delivered by a professional endurance athlete) to maintain a full health pool (300, corresponding to a score of 1000). FIG. 6f shows a simulation of the buffer pool and health reservoir score over time assuming activity varying between 11.5 and 16 MET h per day and 2 days off per week. A perfect health reservoir score of 1000 would require 30 MET h activity per day, as can be seen from the curve in the top right corner of FIG. 6f.

Preferably, the health score is based on a weighted combination of health factor(s) and the exercise record of the person over time. The health factors can be updated regularly by the user. For example, the user can provide health related information after every event that is tracked and processed by the system. The user can update after a meal, after exercising, after weighing himself, etc. In the case of recordal of an activity/event by a sensor, portable device or the like, the captured/calculated parameters can be automatically uploaded and used to produce a revised health score. For example, feedback could be provided showing the effect of exercise while a user is running, working out on exercise equipment etc. In selected embodiments, feedback can be provided to an administrator such as a gym staff member where it is determined that a user is exceeding a predetermined threshold (which due to knowledge of their health can be varied respective to their health score or other recorded data). Accordingly, the health related data can be updated in a near real-time manner.

The user can also update the information twice daily, once daily, or at other periodic times. Moreover, the health score can be based on an average of the information over time. Fitness activity, for example, can be averaged over a period of time (e.g. over a week, month, or year). Averaging data over time will reduce the impact to the health score caused by fluctuations in data. Periods in which the data was uncharacteristically high (e.g., the person was engaging large amount of fitness activity over a short period of time) or uncharacteristically low (e.g., person engaged in no fitness activity for a week due to an illness) does not dramatically affect the health score with averaging over time. The health related information can be stored in the memory or in a database accessible by the processor.

The stored data can also be used to predict future health scores for a user. A prediction module can analyze past data (e.g., fitness habits, eating habits, etc.) to extrapolate a predicted health score based on an assumption that the user will continue to act in a predicable manner. For example, if the data shows that a user has exercised one hour every day for the past thirty days, the prediction module can predict, in accordance with a prediction algorithm, that the user will continue to exercise one hour for each of the next three days. Accordingly, the scoring module can calculate a predicted health score at the end of the next three days based on the information from the prediction module. It can also factor the prediction into other actions. For example, the system can suggest a more exerting physical activity level or challenge to someone who has a high health score but is predicted based on past experience to then take a number of days off for recuperation. Furthermore, the system can provide encouragement to the user to maintain a course of activity or modify behavior. For example, the system can send a message to the user indicating that if the user increased fitness activity by a certain amount of time, the health score would go up by a certain amount. This would allow the user set goals to improve health.

The use of the health score allows for a relative comparison of a user's health with that of another person's even though each person can have very different characteristics, which would make a direct comparison difficult. For example, a first user (User 1) can have a very different body composition or engage in very different fitness activities as compared to a second user (User 2), which makes direct comparison of the relative health of each user difficult. The use of the health score makes comparison of the two users possible with relative ease. In one example, User 1 is slightly overweight, which would tend to lower User 1's health score. However, User 1 also engages is large amounts of fitness activities, thereby raising the user's overall health score. In contrast, User 2 has an ideal body weight, which would contribute to a high health score, but engages in very little fitness activity, thereby lowering the health score. User 1 and User 2 are very different in terms of their health related parameters. Accordingly, it would be very difficult to assess and compare the relative health of User 1 and User 2. In accordance with the invention, information related to certain health parameters is collected from User 1 and User 2, which is used to calculate an overall health score. A comparison of User 1's and User 2's health score allows for an easy assessment and comparison of the health of these two users even though they are very different and have very different habits. Therefore, the health score has significant value so that members of a group can compare their relative health and so that other entities (e.g., employers, health care insurers) can assess the health of an individual. Examples are shown in FIGS. 6d and 6e in which tabular (current) and graphical (historic, current and predicted) scores of different users are shown. As can be seen in FIG. 6e, Katrin is expected to surpass the user (Andre) shortly unless he improves his lifestyle and performance. In FIG. 6d, the impact of the decay algorithm is illustrated to show the effect on the health score of a given user (Andre') and the people he has identified as friends. As noted, user Andre has a current health score of 669 which situates this user between friends Irene (health score 670) and Helle (health score 668). The decay algorithm has acted on all of the health scores shown in the screen shot of FIG. 6d, as indicated in the "Δ1 Day" column. More particularly, most of the friends of Andre have had their health score reduced by 1 point due to the reason of "no activity." A lack of data input to the system is a basis for the processor executing the decay algorithm to determine a "no activity" status for a given user. The one day effect of this status according to the illustrated decay algorithm for most of the users is a reduction of 1 point in one day, and a reduction of 5 points over the course of a week. As such, the decay algorithm can have a tapering, non-linear impact on an overall health score.

As illustrated, user Andre has had moderate activity registered into a memory that is accessible to the system. As a result, the moderate activity is processed and results in a one day change (delta) that is positive, and a change that counteracts the influence of the decay algorithm. Consequently, Andre will be able to observe, as well as the friends that have access to his published health score, that he increased his score from 667 to 669 in one day, and from 662 to its present value over the past seven days as a result of "moderate activity." Moreover, a prediction is computed using the underlying algorithm and an extrapolation of data based on most recent reasons (that is, received data) to increase another 5 points. On the other hand, due to low activity, but a good diet, Helle in the same time period went down 1 point in the last day and a total of 1 point in the last 7 days and is predicted to lose another point if this rate continues. As such, Helle is provided with feedback by execution of the algorithm and the outputs provided by the system which can encourage more activity. On the other hand, Irene has no activity and a poor diet which results in a more aggressive change to her current health score and the longer-view historical and predicted impact on her score. Again, this feedback, which can be provided to users and their friends or to members of a group of users that have associated together for a challenge, etc. to provide individual or team motivation to engage in fitness activities, eat well, and so on.

Moreover, the health score provides an indication of the relative health of the individual without revealing the underlying data used to calculate the health score, which can be sensitive information. For example, a user may be uncomfortable revealing his or her weight, age, or amount of time they spend exercising to others persons or entities. Persons can be embarrassed to share his or her weight or the fact that they virtually never go to the gym. However, since the health score is derived from several factors, the underlying data used to calculate the score is kept private. This feature will facilitate the sharing of the user's overall health because users will not have to disclose private data about themselves. For example, a person may be slightly overweight, but she goes to the gym often. Accordingly, that person can receive a relatively good health score. While the person may not want to disclose her weight, she can still disclose her health score which conveys information about her relative health without disclosing the underlying details. The intrinsic medical parameters (e.g. weight, height, etc.) and the extrinsic physical activity parameters (e.g. exercise duration, frequency, intensity, etc.) are transformed into a masked composite numerical value. The masked numerical value is published while the collected information concerning the intrinsic medical parameters and extrinsic physical activity parameters is maintained private. The underlying intrinsic medical parameters and extrinsic physical activity parameters are protected so that a third party is not able to determine those parameters based on the health score number. This is because the parameters can vary in many different ways and yet the health score number could be the same (e.g., a heavier person that exercises frequently can have the same health score as a person that is not overweight but does not exercise as frequently). Thus, having the health score alone does not reveal a person's health related parameters. Accordingly, the underlying health statistics are masked, yet the health score can be used as a benchmark to indicate a person's health for a variety of applications.

After the scoring module calculates the health score of the user, at step 1270, a publication module recalls from the memory the designated group of recipients that are authorized to receive the health score. The group of recipients can be friends or family of the user, sports teammates, employers, insurers, etc. At step 1280, the publication module causes the health score to be published to the designated group. In the case that the information is to be published to a group of friends, the information can be published to a social networking internet based portal in which access to the data is limited to those designated members of the group.

The health parameter data and health scores can be stored over time, in a memory or other database, so that a user can track his or her progress. Charts can be generated in order for a user to track progress and analyze where there can be improvement in behavior. Moreover, trends can be identified that can lead to the diagnosis of medical problems and/or eating habits. For example, if a person's weight is continuing to increase despite the same or increased amount of fitness activity, the system can trigger or suggest that they seek certain medical tests (e.g. a thyroid test, pregnancy test) to determine the cause of the weight gain.

In certain implementations, the majority of the system is hosted remotely from the user and the user accesses the system via a local user interface device. For example the system can be internet based and the user interacts with a local user interface device (e.g., personal computer or mobile electronic device) that is connected to the internet (e.g., via a wire/wireless communication network) in order to communicate data with the internet based system. The user uses the local interface device to access the internet based system in which the memory and software modules are operating remotely and communicating over the internet with the local device. The local device is used to communicate data to the remote processor and memory, in which the data is remotely stored, processed, transformed into a health score, and then provided to the designated groups via a restricted access internet portal. Alternatively, the system can be primarily implemented via a local device in which the data is locally stored, processed, and transformed into a health score, which is then communicated to a data sharing portal for remote publication to the designated groups.

The system can be implemented in the form of a social networking framework that is executed by software modules stored in memory and operating on processors. The system can be implemented as a separate, stand alone "health themed" social networking system or as an application that is integrated with an already existing social networking system (e.g., Facebook, MySpace, etc.). The user is provided with a homepage in which the user can enter information, manage which information is published to designated groups, and manage the membership of the designated groups. The homepage includes prompts to the user to enter the health related information for the each of the various parameters. The user can enter his or her weight, date of birth, height, fitness activity, and other health related information. The user's health score is then calculated. The health score is shared with other users that are designated as part of a group permitted to have access to that information. Moreover, the user can view the health score information of others in the group. Accordingly, the user is able to compare his or her overall health with the health of others in the group. Comparison of health scores with others in the group can provide motivation to the individuals in the group to compete to improve their health scores. Other information, such as health tips, medical news, drug information, local fitness events, health services, advertising and discounts for medical and/or fitness related supplies and service, issuance of fitness challenges or health related goals, for example, can be provided via the homepage.

In further implementations, the health score can be a composite of a Metric Health Model score and a Quality of Life Model score. Combining scores from multiple models provides a more holistic assessment of a user's health. The Metric Health Model score assesses a user's health based on relatively easily quantifiable parameters (e.g., age, sex, weight, etc.) and compares those numbers to acceptable populations study models. The Quality of Life Model score focus on a user's self-assessed quality of life measure based on responses to a questionnaire (i.e., the system takes into account the user's own assessment of their health and life quality) because there are correlations between how an individual "feels" about his or her life and a realistic measure of health. A combination of the scores from these two models, which will be discussed in more detail below, provides a more inclusive and holistic assessment of health.

The Metric Health Model score is based on medical parameter information of a user, such as their medical history information, attributes, physiological metrics, and lifestyle information to the system. For example, the system can provide the user a questionnaire to prompt responses (yes/no, multiple choice, numerical input, etc.) or provide the user with form fields to complete. Medical history information can include the user's history of medical conditions and/or the prevalence of medical conditions in the user's family. Examples of medical history information can include information such as whether the user has diabetes, has direct family members with diabetes, whether the user or family members have a history of heart attack, angina, stroke, or Transient Ischemic Attack, a history of atrial fibrillation or irregular heartbeat, whether the user or family members have high blood pressure requiring treatment, whether the user or family members have hypothyroidism, rheumatoid arthritis, chronic kidney disease, liver failure, left ventricular hypertrophy, congestive heart failure, regular use of steroid tablets, etc.

The Metric Health Model score can also be based on user attributes. The attributes can include age, sex, ethnicity, height, weight, waist size, etc. In addition, Metric Health Model score can be based on physiological metrics of the user. Examples of physiological metrics can include systolic blood pressure, total serum cholesterol, high-density lipoprotein (HDL), low-density lipoprotein (LDL), triglycerides, high-sensitivity C-reactive protein, fasting blood glucose, etc. The inputs can also include parameters of a user's lifestyle. For example, lifestyle parameters can include inputs about whether the user is a smoker (ever smoked, currently smokes, level of smoking, etc.), how much exercise the user performs (frequency, intensity, type, etc.), type of diet (vegetarian, high-protein diet, low-fat diet, high-fiber diet, fast-food, restaurant, home cooking, processed and pre-packaged foods, size of meals, frequency of meals, etc.). These are some of the examples of parameters that can be used to compare the user's health indicators to survival probability models in order to calculate the user's Metric Health Model score.

Survival probability prediction models can be used to predict the probability that an individual will suffer one or more serious health events over a given time period. Mathematical models can estimate this probability from observed population characteristics. Using observational data on a set of unambiguous severe health events, such as stroke or cardiac infarction, models can generate the probability that an individual will suffer one such event over a given time horizon from a set of measurements of markers, or predictors, for the event (e.g., information about a user's medical history, attributes, physiological metrics, lifestyle, etc. as described above). The time distance between the moment the predictors are measured, and the target event that is generated by such models, is referred to as a survival probability, although it must be understood that not all target events considered are necessarily fatal.

These survival probability models are typically derived from the study of generally large populations that are followed for a considerable length of time, usually more than ten years, and the statistics collected on the observation of the target event(s) are summarized and generalized using mathematical methods. There are a number of such models that exist that have been extensively validated and maintained and improved by periodically updating the model's parameters using new data. Examples of existing models can include a subset of models developed and maintained by the Framingham Heart Study (an extensive bibliography on results obtained from the Framingham Heart study is available at www.framinghamheartstudy.org/biblio), a subset of the models developed and maintained by the University of Nottingham and the QResearch Organization (see, for example, J Hippisley-Cox et al, Predicting cardiovascular risk in England and Wales: prospective derivation and validation of QRISK2, BMJ 336: 1475 doi: 10.1136/bmj.39609.449676.25 (Published 23 Jun. 2008)), the ASSIGN model developed by the University of Dundee (see, for example, H Tunstall-Pedoe et al, Comparison of the prediction by 27 different factors of coronary heart disease and death in men and women of the Scottish heart health study: cohort study; BMJ 1998; 316:1881), the Reynolds model (see, for example, PM Ridker et al, C-Reactive Protein and Parental History Improve Global Cardiovascular Risk Prediction: The Reynolds Risk Score for Men, Circulation 2008; 118; 2243-2251, and Development and Validation of Improved Algorithms for the Assessment of Global Cardiovascular Risk in Women, JAMA, Feb. 14, 2007—Vol 297, No. 6), the PROCAM model from the Münster Heart Study (see, for example, Simple Scoring Scheme for Calculating the Risk of Acute Coronary Events Based on the 10-Year Follow-Up of the Prospective Cardiovascular Münster (PROCAM) Study, Circulation. 2002; 105:310-315), and the SCORE model (see, for example, RM Conroy et al, Estimation of ten-year risk of fatal cardiovascular disease in Europe: the SCORE project, European Heart Journal (2003) 24, 987-1003). Other constituent risk models can also be included. In addition, precursor models can also be used. Precursor models predict the development of a first condition (e.g. high blood pressure), wherein the development of the first condition is predictive of developing a second condition (e.g., heart disease). There are models that generate estimates of the probability of developing diabetes or high blood pressure, for example, which are two important predictors of mortality. A high probability of developing diabetes in five years, for instance, will independently increase the probability of a serious cardiovascular event within the next ten years. Several such precursor models can be included and the inclusion of precursor models leads to more accurate metric risk models, but more importantly, also leads to the possible reduction of the risk of mortality through well-defined modifiable aspects of lifestyle.

Traditional survival probability models have certain inherent limitations that result from the procedures used to build them. In deriving such models, researchers compromise between accuracy and usability. It is difficult for an inductive model, meaning a model derived directly from data, to include all possible predictors. This is in part because not all relevant predictors of a particular event are known, but also in part because some known predictors may be difficult or expensive to measure. In fact, several well-known markers of risk, such as genetic factors, are often not included in such models. Therefore, several potential and known predictive metrics can be excluded as covariates when deriving a given survival model.

Survival probability models are built using data collected from a given population, and thus summarize and generalize morbidity and mortality characteristics of the studied population. However, such a model might be at variance when compared with risk estimates derived from other populations. When a given model is used in a population that differs from the one where the model was built it often underestimates or overestimates a particular risk because only a few predictors are often considered, and because other relevant predictors that may not be included in the model might very well differ between two populations.

Given the above discussion, together with basic probabilistic logic, a judicious combination of models derived for several different populations will generate a better view of the risks that an individual picked at random is exposed to, and will thus be more robust in estimating risks for the population at large. Furthermore, based on mathematical grounds, under very general assumptions, certain model combination methods, referred to as predictor boosting, can improve the accuracy of the constituent models. In fact, boosting a set of models, when done correctly, will produce a model with accuracy that is, at worst, equal to that of the most accurate model in the boosted set.

Accordingly, the Metric Health Model score can be calculated by comparing the user's medical parameter information to the survival probability models. A score, preferably in the range of 0 to 1000, with the top end signifying perfect health and the low side signifying poor health, can be derived following a two-step process. First, an overall survival probability is obtained from a combination of the survival probabilities generated by individual survival probability models, as described above. Second, the resulting survival probability, which is a number in the 0 to 1 range, is transformed using a parametric nonlinear mapping function into the 0 to 1000 range. The parametric mapping function is tuned so that it is linear, with a high slope, in the region of typical survival probabilities, and asymptotically slopes off in the low and high ends of the survival probability distribution. The mapping function is designed to be strongly reactive to changes in the typical survival probability region.

As discussed above, the health score can be composed of the Metric Health Model score, and also the Quality of Life Model score. The Quality of Life Model score is based on a user's answers to a set of questionnaires. The system can include several different questionnaires with some questions in common. The type of questionnaires and the type of questions therein presented to the user can be tailored based on a user's health parameters (i.e., user age, other data in the user's medical history, etc.). A specific questionnaire can be generated and presented to the user on the basis of information on the user that is known to the system. The questions can be presented with an appropriate multiple choice response that the user can check/tick on a form, with no free-form text is entered by the user to permit easier assessment of the responses. Other types of responses are possible (e.g., rating how true a statement is to the user 1-10). The following list provides several sample questions (in no particular order) on a number of health-related quality of life topics that can be used in a system questionnaire.

Sample Questions:
How do you rate your quality of life?
How do you rate your overall health?
How much do you enjoy life?
To what extent do you feel your life to be meaningful?
How well are you able to concentrate?
How safe do you feel in your daily life?
How healthy is your physical environment?
Are you satisfied with your appearance?
To what extent do you have the opportunity for leisure activities?
How much do you need any medical treatment to function in your daily life?
For how long have your activities been limited because of your major impairment or health problem?
Do you need help in handling your personal care needs because of health problems?
Do you need help in handling your routine needs because of health problems?
Are you limited in any way in any activities because of any major impairment or health problem?
How true or false is each of the following statements for you?:
 I seem to get sick a little easier than other people
 I am as healthy as anybody I know
 I expect my health to get worse
 My health is excellent
Do you suffer from any of the following major impairment or health problem that limits your activities?:
 Arthritis or rheumatism
 Back or neck problem
 Cancer
 Depression, anxiety or any emotional problem
 Vision problem
 Fractures, bone/joint injury
 Hearing problem
 Breathing problem
 Walking problem
 Other impairment or problem
During the past 30 days, for about how many days:
 was your physical health not good?
 did pain make it hard for you to do your usual activities, such as self-care, work, or recreation?
 have you felt sad, blue or depressed?
 have you felt worried, tense or anxious?
 have you felt you did not get enough rest or sleep?
 have you felt very healthy and full of energy?
 have you been a very nervous person?
 have you felt so down in the dumps that nothing could cheer you up?
 have you felt calm and peaceful?
 did you have a lot of energy?
 have you felt downhearted and blue?
 did you feel worn out?
 have you been a happy person?

did you feel tired?
How satisfied are you with:
your sleep?
your ability to perform your daily living activities?
your capacity for work?
yourself?
your personal relationships?
your sex life?
the support you get from your friends?
the conditions of your living place?
your access to health services?
your transport?
Are you limited in any of the following activities because of your health?:
Vigorous activities, such as running, lifting heavy objects, participating in strenuous sports
Moderate activities, such as moving a table, pushing a vacuum cleaner, bowling, or playing golf
Lifting or carrying groceries
Climbing several flights of stairs
Climbing one flight of stairs
Bending, kneeling or stooping
Walking more than a mile
Walking several blocks
Walking one block
Bathing or dressing yourself This list above is just a sample of questions that can be presented to a user. The user's responses to the questions are assigned a value. For example, each of the multiple choice responses can be assigned a particular value, and all of the user's response can be tallied to generate a score. In addition, different questions and different responses can be weighted differently since some questions, or the severity of the response, can have a greater predictor of the user's health. The system can also assign a value based on the user's response to a combination of questions, because certain combinations can be more predictive of health. Accordingly, by assessing the user's responses to the questionnaire a Quality of Life Model score can be derived. Preferably, the Quality of Life Model score is a numerical value in the range of 0 to 1000.

The health score is computed as a weighted average of the Metric Heath Model score and the Quality of Life Model score. The health score can presented to the user. The health score can be presented as a numerical value, as a graphic value (i.e. as a meter, bar, or slider), or a combination of the both, for example. Referring to FIG. 6A, the health score is presented by a combination of a numerical score 1302 and a slider 1304. The slider can also be color-coded to indicate the score. The position of the slider bar 1306 indicates the user's score.

One advantage of the presentation of the health score is that it is not necessary to present the survival probabilities and raw metrics to the user. Instead, users are presented with a standardized score. Preferably, this is true of the overall Metric Heath Model and Quality of Life scores, but it is also true of the relevant model inputs. This is done mainly to standardize all output, in the sense that users do not need to know whether high values of a particular input variable are good or bad; in all cases, high scores of any input value lead to higher overall health score values, and low input variable scores lead to lower overall values of the health score.

Furthermore, another advantage of the standardized health scores is that users can compare health scores against other users. This allows for comparative bench marking (against friends, co-workers, etc.) with other users. Such score comparisons can be a part of a game component of the system in which the user competes against other users, as will be described in more detail below. Gaming aspects of the system can be used motivate the user of the health score system, such as a comparison of scores among user-selected groups, comparison of individual scores within configurable subpopulation distributions, time-tracking of scores, and setting of goals, among others. Referring to FIG. 6B, the users numerical score 1302 and graphical score 1306 are presented in combination with a range of scores 1308 from a group (e.g. the world) so that the user can see how his/her score compares to others in the group. The gaming incentives can be extended by users to allow the comparison of health scores between users that can differ substantially in one or more of several specific input parameters, such as age, weight, and prior risk conditions. The system highlights improvements in modifiable user metrics, particularly in lifestyle components, and these improvements in score provide user incentives. This allows fair competition between users of a father and his children, for example, via the health score. In one aspect, the health score provides equalization between users of different characteristics and is thus similar to that of a handicap in some sports. Referring to FIG. 6C, the user's score 1306 is compared to the scores 1310*a-e* of a user selected group of friends. Referring to FIG. 6D, the user's individual medical parameters (e.g., the medical data provided as a part the Metric Health Model) can be compared against other users graphically without revealing the underlying actual values. The high-density lipoprotein (HDL) level, low-density lipoprotein (LDL) level, systolic blood pressure (sBP), diastolic blood pressure (dBP), body mass index (BMI), and fasting blood glucose (fBG) level are shown on a graph 1312. The user's scores are represented by a line 1314, the user's friends scores are each represented by a different dot 1316, and a distribution block 1318 for a larger population group (e.g., Switzerland) is also shown. Thus, the user can compare their individual parameters to a group of friends and the average for a large population group.

Users can input data into the system at the time of an event (i.e., exercise event, food consumption, blood pressure measurement, etc.), and see the resulting update of their health score in real-time. The system can include drill-down capabilities, allowing users to see the various health score component scores, including tracking over time and the corresponding trends in all scores; it also includes the setting of goals on the various scores.

As an example of use of the system, upon registration with the system (e.g., the initial use of the system), a user is prompted to provide medical history data. The user is also prompted to respond to a complete Quality of Life questionnaire selected by the system for the given user based on the medical history and user parameters supplied by the user. After the registration, at periodic intervals, users are presented with short subsets (3 to 5 questions) of their custom Quality of Life questionnaire to keep their responses up to date and track changes. Users can enter inputs for Metric Health Model at any time, and the system prompts the user for values that have not been updated for some time. Inputs to the Metric Health Model can be acquired automatically by the system by accessing a series of digital measuring devices that have been integrated into the system (e.g., the system can comprise a mobile electronic communication device, for example, a smart phone, that is in wireless communication with a measurement device, such as a blood glucose monitor, so that parameters can be measured, transmitted, and stored by the system). These can include weight, blood glucose, physical activity, and other parameters. Several or multifunction digital measurement devices can be included in the system. In the case of medical parameters that are more difficult to obtain with a home measuring device, such as serum lipid concentration levels, users are only prompted to provide the relevant data once per (system) configured time period (e.g., annually and coinciding with a user's routine physical medical examination).

To avoid false scores, the system can include several algorithms to assess the validity of user inputs. The validation methods can range from ones based on outlier detection to ones based on multidimensional likelihood estimators. When the system detects a possible bad input value it flags it and prompts the user to either confirm the value or to enter a new one.

The system can generate all its scores, even when missing one or more inputs. It does this by imputing the missing value or values using a variety of statistical methods that range from ones based on global population statistics, to methods based on the use of more complicated statistical models that are built into the platform. However, whenever inputs include imputed values, the system clearly flags all affected scores, and periodically alerts the user to provide the missing data. The system can also allow for score simulation, in which the user can temporarily adjust his or her parameters so that a user can see how changing certain parameters (e.g., losing weight) affects the user's score.

The system can also provide recommendations to the users to take certain actions that can improve the user's health score. These recommendations can be very specific when any input variable is in its danger zone, and more generic when any input variable is outside its optimal range.

As discussed above, the health score can be used as a part of a game or competition aspect of the system. The game aspect increases the fun element of the system for the user and increases the user's affinity to continue to use the system. The game aspect can come in the form of obtaining higher levels based on achievements, competing against others (e.g., in a league), and/or completing challenges. The "level" is an overall indication of progress. The level can be monotonically increasing and will increase by gaining activity points. Activity points can be gained from performing numerous activities, such as time spent performing fitness activities (e.g., exercising), improving one's health score, improving one's BMI, taking part in discussions on the system (e.g., the system can be a web-based social networking platform and discussions or "classes" can be offered to teach fitness skills). A user's level can be displayed on a user's profile and in discussion posts so that other users can see each other's level. A user's level status can also provide access to specific items, system features and functionality, or rewards (e.g., branded apparel).

Users can also compete within leagues in the system. The leagues are composed of groups of users and the users within the league can compete against each other (as part of a team or individually). The leagues can compete for a limited time (e.g., monthly) and the leagues can be designated based on the level of the users (using the level of the user as discussed above), the type of activity being performed in the league, and the geographic region of the users. For example, one particular league can be the "bronze" (level) "mountain biking" (sport) "Greater Zurich Area" (region) league and a user's success in this league is measured by the distance traveled and elevation climbed (measured quantity). Thus, bronze level users living in the Greater Zurich Area that are interested in mountain biking can compete in this league. Limiting the leagues to a particular region gives the users something to relate with and all the users can share in common, and further allows users to meet face to face (e.g., for group exercise events). One issue with one big international league is that such a league may seem anonymous, crowded and meaningless to some users (members competing against members residing on completely different continents with language barriers can inhibit group or team mentalities). Limiting leagues to particular level brackets equalizes the playing field for users of particular skill levels. Quantities to be measured to determine performance in the league can include distance (horizontal, vertical) and duration of fitness activity performed, for example. Users can also form teams within the leagues. Team leagues work in the same way as the leagues outlined above, however the ranking is based on the team's overall performance. Teams increase the communal aspect of participation in the activity. Teams can be fixed in size (e.g., 2, 3, 5, 10, etc. users).

Users can also be presented by the system with challenges to complete. The challenges can set forth a time period for completion of a goal. The goals of the challenge can be, for example, healthscore improvement (normalized), completion of sport-related activity parameters (e.g., total distance, total climbing, etc.), or completion of a sport-related activity within a specific period of time (e.g., complete six minute mile on a specific route). The challenge can be public and any user can participate, or limited to a group (e.g. friends, co-workers, social group, etc.) As an example, a particular public challenge can be an inline skating challenge in New York City for the route around the Central Park Loop measuring the time taken for completion. Public challenges can be generated automatically by the system or by system administrators. Group challenges can be issued by group members. Challenges provide strong appointment dynamics, encouraging users to commit to exercise. Challenges (typically) have a lower time commitment than leagues. Route selection can be automated with the community. In a first step, the community can publish routes on the system platform (e.g., a social networking type website); in a second step, the system selects popular routes (i.e. routes with high user activity) as weekly challenges. Route validation is done by GPS tracking. Challenges can be safety screened to prevent the promotion of unduly risky challenge activities, such mountain biking dangerous downhill routes.

The league and challenge systems provide opportunities to grant achievements. Achievement status indications can be collected and displayed on a user's profile. Achievements are much like a trophy, medal, or award provided to the user for completing challenges and/or succeeding in a league activity. Many different achievements are possible, such as related to the number of friends the user has on the system (community participation), achievements related to the time, intensity, and number of fitness activities engaged in (level of fitness participation), achievements related to specific sport activities (e.g., distance run), the frequency a user measures their parameters (e.g., weight) in order to keep the system up to date, the amount of weight lost, or the ability to maintain ones BMI, for example. The following list is an exemplary set of achievements and the activities required to earn the achievements:

Exemplary Achievement List:
Challenger: Take part in a public challenge.
Accomplished Challenger: Take part in 10 public challenges.
Champion: Win a challenge.
Multi-sport Champion: Win a public challenge in two different sports.
International Challenger: Take part in a public challenge in two different countries.
International Champion: Win a public challenge in two different countries.

World Wide Challenger: Take part in a public challenge on each continent.

World Wide Champion: Win a public challenge on each continent.

Other aspects of the challenge and league systems are that the systems can be tied to marketing opportunities. For example, marketers can sponsor prizes for the winners of a challenge. The prize can be related to the challenge (e.g., gift certificate to health food score for winner of weight loss challenge). In addition, challenge routes can be selected to direct users to certain areas to increase tourism or to begin/end at selected destinations (e.g., bike challenge begins in front of sports equipment store).

One advantage of the system is that it provides users and groups of users with benchmarking capabilities. It allows other groups, such as insurance carriers or employers, to assess the relative health of individuals in order to determine the health related risks of each individual. Accordingly, users can compare themselves against others in order to assess their comparative health level amongst a group of friends. Insurance carriers can use the health score information to set premiums for an individual or a group of individuals (e.g. employees of a company). In other implementations, health scores can be provided for a group based on the health scores of the individuals in the group. For example, a health score can be calculated for a company based on its employees so that an insurance carrier can set premiums based on the health score of the company compared to other companies. In further applications, the health score can be used for assessing the health of professional athletes to determine the athlete's real market value. Vast amounts of money and resources are invested in athletes at all levels in professional sports. A large component of the decision about investing in an athlete is based on the past performance of the athlete. Other factors can include past physical injury history and the athlete submitting to a physical exam before the deal is complete. The health score can be used as an indicator of the athlete's current health and used as a predictor of the athletes future performance. If the athlete's health score were low, this can indicate that the athlete is more prone to suffering an injury or that physical performance will diminish. Accordingly, the health score can form a basis for a decision on whether to invest in an athlete. The health scores could also be used as a predictor of the outcome of a particular game played between two teams. For example, the health scores of the individual team members can be aggregated in order to provide a team health score. A comparison of the team health scores can be indicative of the likely outcome of the game between the two teams (e.g., the team with highest health score may be more likely to win). Such information can be used in gaming contexts such as fantasy sports teams, or in order to set odds for sports betting. The health score could be used for club competitions (e.g., group health improvement competitions, advertising based on a person's health score, gaming, tv/internet, etc.

Thus, in a broad aspect, a method according to the invention can be understood as collecting health related information, processing the information into a health score, and publishing the health score is provided. A system for implementing the method can include a computer having a processor, memory, and code modules executing in the processor for the collection, processing, and publishing of the information. Information concerning a plurality of health related parameters of a user is collected, particularly, both intrinsic values concerning the measurable, medical parameters of at least one natural person, and the extrinsic values concerning the activities of each such person(s) such as the exercise performed, the type of job the person has and the amount of physical work associated with the job (e.g. sedentary, desk job versus active, manual labor intensive job) and/or the calories/food consumed. Weighting factors are applied to the health related parameter in order control the relative affect each parameter has on the user's calculated health score. The health score is computed using the processor by combining the weighted parameters in accordance with an algorithm. The health score is published to a designated group via a portal. In one implementation, the portal is an internet based information sharing forum.

As such, the invention can be characterized by the following points in a method for collecting and presenting health related data:

collecting information concerning a plurality of health related parameters of a user;

storing the collected information in a memory;

storing weighting factors in the memory;

processing the collected information by executing code in a processor that configures the processor to apply the weighting factors to the health related parameters;

computing a health score using the processor by combining the weighted parameters in accordance with an algorithm; and providing the health score to a designated group via a portal.

The methods described herein have been described in connection with flow diagrams that facilitate a description of the principal processes; however, certain blocks can be invoked in an arbitrary order, such as when the events drive the program flow such as in an object-oriented program implementation. Accordingly, the flow diagrams are to be understood as example flows such that the blocks can be invoked in a different order than as illustrated.

While the invention has been described in connection with certain embodiments thereof, the invention is not limited to the described embodiments but rather is more broadly defined by the recitations in any claims that follow and equivalents thereof.

The subject matter described above is provided by way of illustration only and should not be construed as limiting. Various modifications and changes can be made to the subject matter described herein without following the example embodiments and applications illustrated and described, and without departing from the true spirit and scope of the present invention, which is set forth in the following claims.

We claim:

1. A computer-implemented method for managing data corresponding to a user's activity and health, and providing a corresponding masked composite numerical value to the user through a portal, the method comprising:

capturing, by an electronic image capture device, an image having a set of pixels of an exercise machine display that is separate from the image capture device;

configuring, by a processor, a control circuit to gather from a memory that is operatively and wirelessly connected to the control circuit, image data from the image;

comparing, by using the configured processor to implement a photo comparison algorithm, the image data to at least one other image that corresponds, within a predetermined degree of similarity, to the image to determine a make and model of the exercise machine depicted as a function of the image data;

automatically selecting, using the configured processor and as a function of the determined make and model of the exercise machine, a particular portion of the set of pixels in which information representing extrinsic physical activity parameters associated with physical activity of the user is represented, wherein the particular portion has fewer pixels than the set;

identifying, using the configured processor, sequences of characters within the particular portion of pixels;

determining, using the configured processor, spatial relationships between the sequences only within the particular portion of the pixels;

defining, using the configured processor, one or more data unit types in accordance with the identified sequences and/or determined spatial relationships;

determining, using the configured processor, a measure of calories expended in the physical activity;

generating, using the configured processor, extrinsic physical activity parameter data associated with the extrinsic physical activity parameters that is located within the selected particular portion of pixels as a function of the defined data unit types and determined measure of calories;

updating, using the configured processor, a stored profile associated with the user that includes previously captured data with at least some of the generated extrinsic physical activity parameter data;

receiving, by a data collection module executed by the configured processor, a plurality of intrinsic medical parameters of the user that include the user's body weight, and storing the intrinsic medical parameters in the memory;

applying, by a weighting module executed by the configured processor, at least one respective weighting factor that is recalled from the memory to at least one of the intrinsic medical parameters to calculate at least one weighted intrinsic weighted parameter;

transforming, by the configured processor, the measured calories into a metabolic equivalent value by dividing by the user's body weight;

allocating, by the configured processor, the metabolic equivalent value among a health pool and a bonus pool, wherein the bonus pool has a predetermined size and wherein the metabolic equivalent value is allocated to the bonus pool up to the predetermined size, and any metabolic equivalent value exceeding the bonus pool size is allocated to the health pool;

applying, by the weighting module executed by the configured processor, at least one weighting factor to a health pool value to calculate a weighted health pool value;

transforming, by the configured processor, the intrinsic medical parameters and the extrinsic physical activity parameters into a masked composite numerical value by combining at least the weighted intrinsic medical parameters and the weighted health pool value in accordance with an algorithm;

publishing, by the configured processor, the masked composite numerical value to the user through the portal, wherein the portal comprises a web-based portal accessible through the internet or an application on a mobile computing device; and enabling the user to view the masked composite numerical value using the mobile computing device.

2. The method of claim 1, further comprising using an optical character recognition algorithm on the captured image.

3. The method of claim 1, further comprising a step of extracting, using the configured processor, text from a particular portion of the pixels.

4. The method of claim 1, further comprising the steps of:
automatically publishing the masked composite numerical value to a designated group via the portal, using code executing in the configured processor and free of human intervention, while maintaining the collected information concerning the intrinsic medical parameters and the extrinsic physical activity parameters private.

5. The method of claim 4, wherein the at least one weighting factor includes a decay component arranged to reduce a relative weight of the extrinsic physical activity parameters for a physical activity in dependence on at least one factor associated with the user.

6. The method of claim 5, wherein the at least one factor associated with the user is an age or an age range of the user such that the decay component reduces the relative weight for a first user of a first age or age range differently than a second user of a second age or age range.

7. The method of claim 1, wherein the steps of transforming, allocating and publishing are performed substantially automatically upon receipt of data on intrinsic medical parameters or extrinsic parameters of a user.

8. The method of claim 1, further comprising:
automatically establishing an exercise program at the exercise machine using a log of the user's past physical activity.

9. The method of claim 1, further comprising
executing further code in the processor that configures the processor to:
apply a daily decay component to the bonus pool.

10. The method of claim 1, further comprising sorting, as a function of a sequencing algorithm, optical character recognition data into categorized sequenced data.

\* \* \* \* \*